United States Patent
Fujimoto et al.

(10) Patent No.: US 10,844,087 B2
(45) Date of Patent: *Nov. 24, 2020

(54) METHOD OF SUPPRESSING FORMATION OF PHOTOCROSSLINK, AND PHOTOREACTIVE NUCLEIC ACID IN WHICH AUTO-CROSSLINK FORMATION IS SUPPRESSED

(71) Applicant: JAPAN SCIENCE AND TECHNOLOGY AGENCY, Kawaguchi (JP)

(72) Inventors: Kenzo Fujimoto, Nomi (JP); Shigetaka Nakamura, Nomi (JP)

(73) Assignee: JAPAN SCIENCE AND TECHNOLOGY AGENCY, Kawaguchi (JP)

(*) Notice: Subject to any disclaimer, the term of this patent is extended or adjusted under 35 U.S.C. 154(b) by 493 days.

This patent is subject to a terminal disclaimer.

(21) Appl. No.: 15/033,422

(22) PCT Filed: Oct. 30, 2014

(86) PCT No.: PCT/JP2014/078980
§ 371 (c)(1),
(2) Date: Apr. 29, 2016

(87) PCT Pub. No.: WO2015/064718
PCT Pub. Date: May 7, 2015

(65) Prior Publication Data
US 2016/0326207 A1  Nov. 10, 2016

(30) Foreign Application Priority Data

Oct. 30, 2013 (JP) .................. 2013-225799

(51) Int. Cl.
| | | |
|---|---|---|
| *C07H 19/06* | (2006.01) | |
| *C07H 19/04* | (2006.01) | |
| *C07H 21/04* | (2006.01) | |
| *C07H 19/073* | (2006.01) | |
| *C07H 19/10* | (2006.01) | |
| *C07H 19/044* | (2006.01) | |

(52) U.S. Cl.
CPC ............ *C07H 19/06* (2013.01); *C07H 19/04* (2013.01); *C07H 19/044* (2013.01); *C07H 19/073* (2013.01); *C07H 19/10* (2013.01); *C07H 21/04* (2013.01); *C12Q 2525/101* (2013.01); *C12Q 2525/117* (2013.01)

(58) Field of Classification Search
CPC ...... C07H 21/04; C07H 19/04; C07H 19/073; C07H 19/06
See application file for complete search history.

(56) References Cited

U.S. PATENT DOCUMENTS

| | | | | |
|---|---|---|---|---|
| 4,458,066 A * | 7/1984 | Caruthers | ............ | B01J 19/0046 536/25.34 |
| 5,132,418 A * | 7/1992 | Caruthers | ............ | B01J 19/0046 536/25.3 |
| 7,972,792 B2 * | 7/2011 | Fujimoto | ............... | C07H 21/04 435/6.11 |
| 8,481,714 B2 * | 7/2013 | Fujimoto | ............. | C07D 405/04 536/26.9 |
| 8,658,780 B2 * | 2/2014 | Pierce | ................... | C12N 15/111 435/6.12 |
| 9,771,612 B2 * | 9/2017 | Hori | .................... | G01N 21/6428 |
| 9,925,277 B2 * | 3/2018 | Almarsson | ............. | A61K 38/00 |
| 9,944,979 B2 * | 4/2018 | Terasaki | ............... | C12Q 1/6858 |
| 10,023,626 B2 * | 7/2018 | Bolen | .................... | A61K 48/00 |
| 2010/0274000 A1 | 10/2010 | Fujimoto et al. | | |
| 2013/0177918 A1 | 7/2013 | Terasaki et al. | | |
| 2015/0211057 A1 | 7/2015 | Wakamatsu et al. | | |
| 2016/0031918 A1 | 2/2016 | Fujimoto et al. | | |

FOREIGN PATENT DOCUMENTS

| | | |
|---|---|---|
| EP | 2 272 856 A1 | 1/2011 |
| WO | 2009/066447 A1 | 5/2009 |
| WO | 2012/033190 A1 | 3/2012 |
| WO | 2014/014106 A1 | 1/2014 |

(Continued)

OTHER PUBLICATIONS (R) Inoue et al., "Nucleosides and Nucleotides. XXI. Synthesis of 6-Cyano- and 5-Cyanouritidines and Their Derivatives," Chemical & Pharmaceutical Bulletin, 26(9), 2657-2663 (1978).*
(S) Heinrich et al., "Lys314 Is a Nucleophile in Non-Classical Reactions of Orotidine-5'-Monophosphate Decarboxylase," Chemistry—A European Journal, 15(27), 6619-6625 (Jun. 29, 2009).*
(T) H. Gobind Khorana, "Some Recent Developments in the Chemistry of Phosphate Esters of Biological Interest," Chapter 2 (Synthesis of Monoesters of Phosphoric Acid), John Wiley & Sons, New York, NY, 1962, only pp. 13-43 supplied.*

(Continued)

*Primary Examiner* — Eric Olson
(74) *Attorney, Agent, or Firm* — Westerman, Hattori, Daniels & Adrian, LLP

(57) ABSTRACT

Provided is a means for preventing the inactivation of a photoresponsive nucleic acid probe by suppressing the formation of a photocrosslink between a modified nucleotide having a structure corresponding to the monomer of Formula (II) or an amino acid analogue of a nucleotide having a structure corresponding to the monomer of Formula (III) and a modified nucleotide having a structure corresponding to the monomer of Formula (I), wherein the modified nucleotide replaces at least one constituent nucleotide which is the photocrosslinkable 1-thyminyl or 1-uracilyl, by substituting at least one constituent nucleotide which is the photocrosslinkable 1-thyminyl or 1-uracilyl with a modified nucleotide having a structure corresponding to the monomer of Formula (I).

50 Claims, 7 Drawing Sheets

Specification includes a Sequence Listing.

(56) References Cited

FOREIGN PATENT DOCUMENTS

WO    WO2014/093924    *   6/2014
WO      2014/157565 A1    10/2014

OTHER PUBLICATIONS

Guschilbauer et al., "Oligonucleotide Conformations" Auropean Journal of Biochemistry vol. 32 pp. 1-13 (Year: 1972).*
Beaucage, L Serge, "2-Cyanoethyl tetraisopropylphosphoramidite", p. 5, from Encyclopedia of Reagents for Organic Synthesis (Year: 2003).*
Notification of Transmittal of Translation of the International Preliminary Report on Patentability (Form PCT/IB/338) issued in counterpart International Application No. PCT/JP2014/078980 dated May 12, 2016 with Forms PCT/IB/373 and PCT/ISA/237. (5 pages).
Crouch et al.,"Synthesis of 2'-Deoxyuridine Nucleosides With Appended 5-Position Carbonyl Cross-Linking Groups", Nucleosides & Nucleotides, 1994, vol. 13, No. 4, pp. 939-944, Cited in ISR.
Gai, et al., "A Sensitive Multispectroscopic Probe for Nucleic Acids", Journal of Physical Chemistry B, 2010, vol. 114, No. 23, pp. 7958-7966, Cited in ISR.
International Search Report dated Dec. 2, 2014, issued in counterpart International Application No. PCT/JP2014/07980 (2 pages).
Extended (supplementary) European Search Report dated Apr. 19, 2017, issued in counterpart European Application No. 14858942.7. (7 pages).

* cited by examiner

Fig. 4
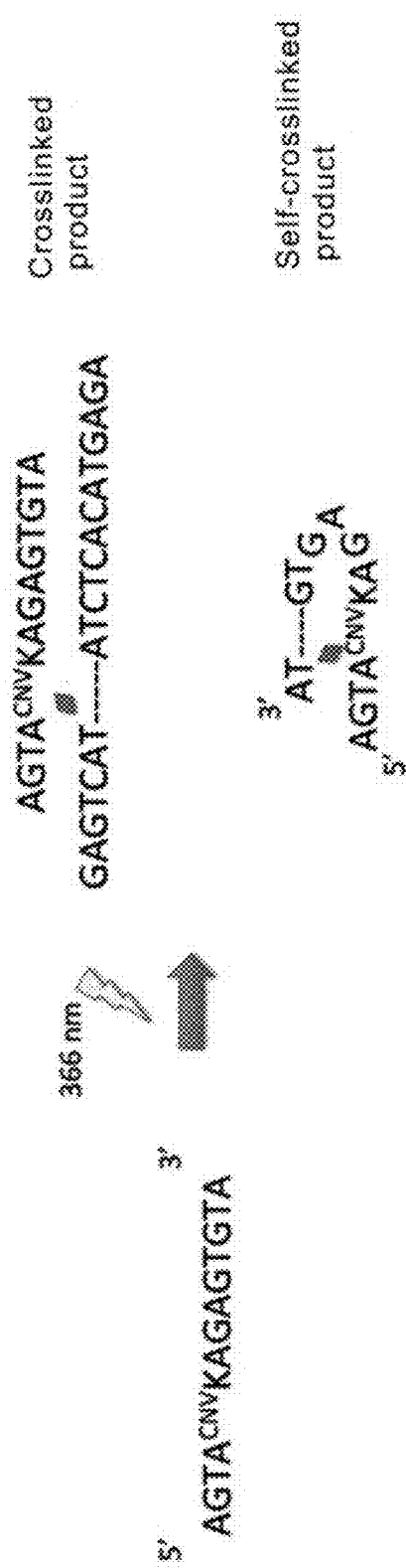
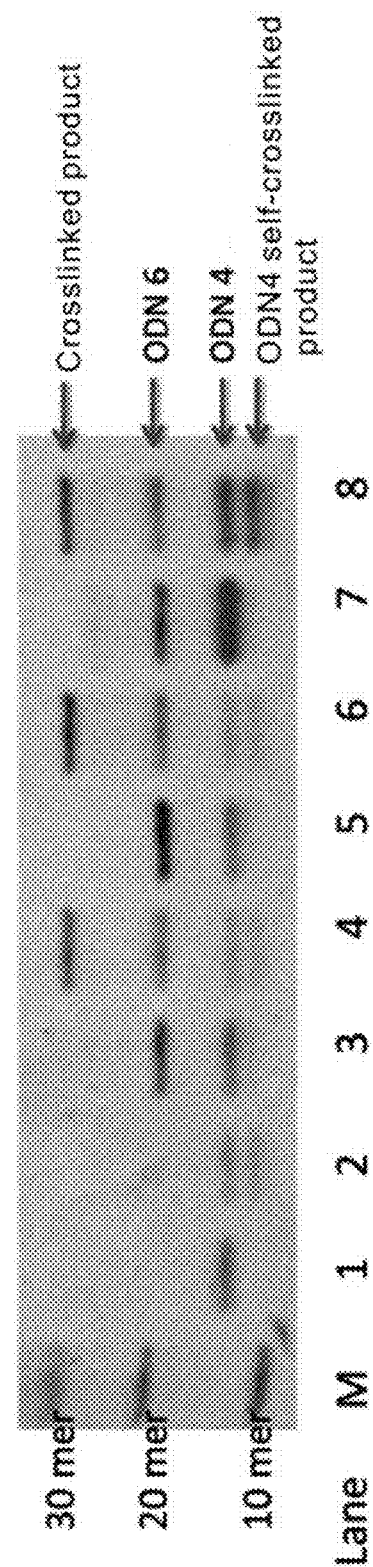

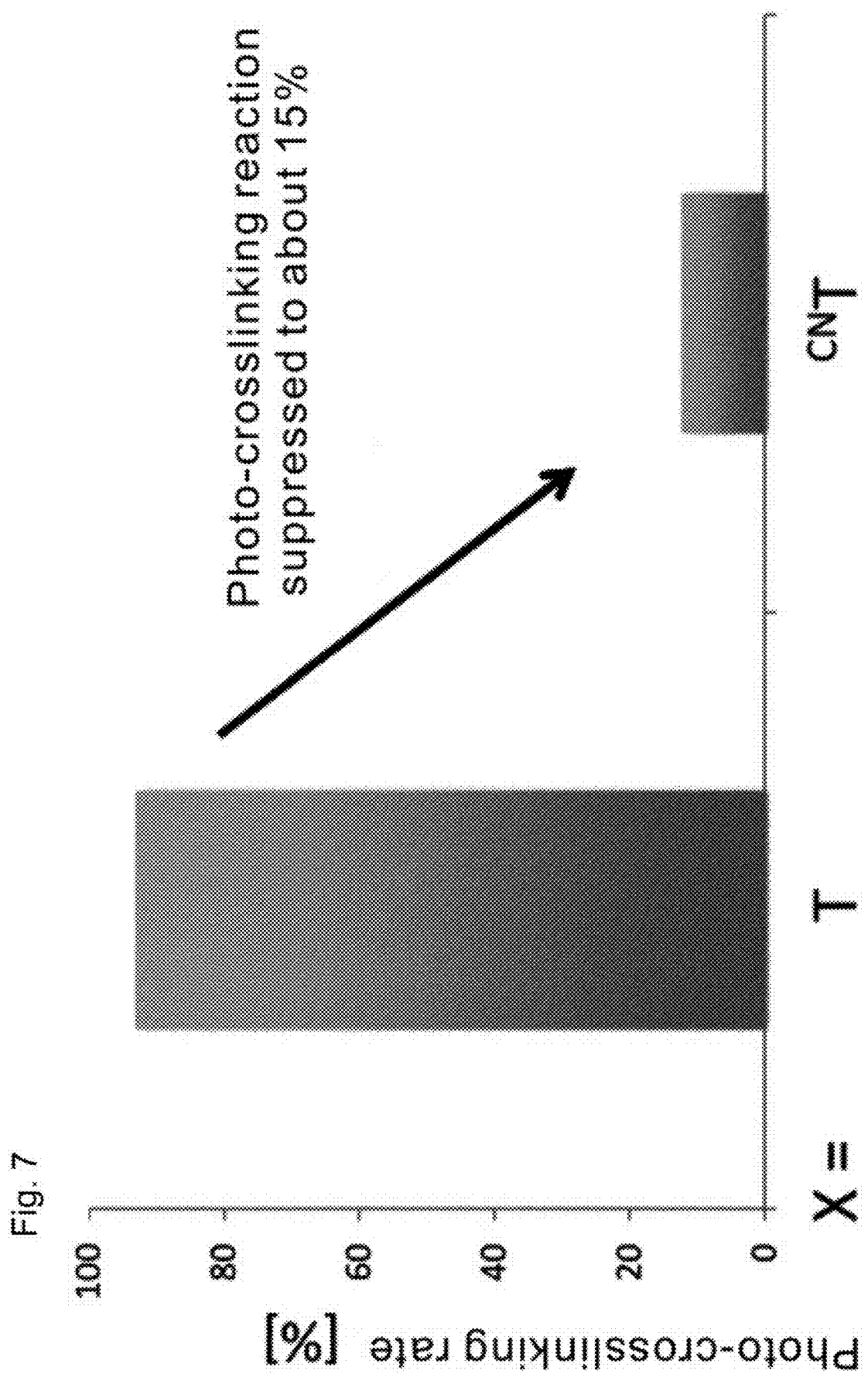

ined photoresponsive nucleic-acid probe. The photo-crosslinking technique with the use of photoresponsive nucleic acids has been developed by the inventors of the present invention and their research group, and a plurality of artificial photoresponsive nucleotides have been developed and are under patent pending (Patent Document 1).

METHOD OF SUPPRESSING FORMATION OF PHOTOCROSSLINK, AND PHOTOREACTIVE NUCLEIC ACID IN WHICH AUTO-CROSSLINK FORMATION IS SUPPRESSED

CROSS-REFERENCE TO RELATED APPLICATIONS

This application is a national stage of international application no. PCT/JP2014/078980, filed Oct. 30, 2014, and claims priority to Japanese application no. 2013-225799, filed Oct. 30, 2013, the entirety of all of which are herein incorporated by reference.

FIELD

The present invention relates to a method of suppressing photo-crosslinkage of a photoresponsive base having a photo-crosslinkable vinyl structure with a photo-crosslinkable thymine (T) or uracil (U) base, and also relates to a photoresponsive nucleic acid with suppressed self-crosslinking ability.

BACKGROUND

As a basic technique in the field of molecular biology, formation and detection of a double strand of nucleic acids are widely used not only in basic research but also in the fields of medical care, industry, agriculture, and the like. A particularly useful technique used in formation and detection of a double-stranded nucleic acid is the photo-crosslinking technique with the use of photoresponsive nucleic acids. The photo-crosslinking technique is used in a wide range of applications, for example, in the field of medical care including antisense drugs and other nucleic acid drugs as well as SNP sensing, and the field of DNA nanotechnology with the use of nucleic acids. The photo-crosslinking technique with the use of photoresponsive nucleic acids has been developed by the inventors of the present invention and their research group, and a plurality of artificial photoresponsive nucleotides have been developed and are under patent pending (Patent Document 1).

One of the most remarkable applications of the photo-crosslinking technique is highly-sensitive selective amplification of a nucleic acid (the photo-clamping method) (Patent Document 2). This is a method of, prior to PCR amplification of a nucleic acid, using a photoresponsive nucleic acid as a clamp probe and subjecting the clamp probe to photo-linkage with a nucleic acid that has a wild-type (or normal) base sequence and is present in a large number in a specimen, so as to form an indissociable double-stranded nucleic acid, and as a result, suppressing PCR amplification of the large number of nucleic acid having a wild-type (or normal) base sequence, thereby allowing selective and highly sensitive amplification of a nucleic acid that has a target mutant base sequence and is present in a small amount in the specimen.

CITATION LIST

Patent Literature

Patent Literature 1: International Publication No. WO 2009/066447
Patent Literature 2: International Publication No. WO 2012/033190

SUMMARY

Technical Problem

The inventors of the present invention and their research group encountered a problem related to the photo-clamping method: a photoresponsive nucleic acid sometimes fails to fully exhibit its function as a clamp probe or becomes partly inactive, resulting in decreased efficiency in clamp formation, although such a phenomenon should not have occurred considering the high photoreactivity of the photoresponsive nucleic acid. This inactivation of the photoresponsive nucleic-acid probe not only decreases the efficiency of the photo-clamping method but also can cause problems in any of the applications of photoresponsive nucleic-acid probes.

An object of the present invention is to provide a means for preventing inactivation of a photoresponsive nucleic-acid probe.

Solution to Problem

The inventors of the present invention have conducted intensive research and, as a result, have found that inactivation of a photoresponsive nucleic-acid probe in the photo-clamping method occurs when the base sequence of the photoresponsive nucleic-acid probe is capable of forming a double-stranded section within the base sequence: in which case, the photoresponsive nucleic-acid probe containing a double-stranded section within the base sequence undergoes photo-crosslinkage, in other words, the photoresponsive nucleic-acid probe undergoes self-crosslinkage, and consequently loses its intended ability to form a double strand with a complementary strand and then undergo photo-crosslinkage.

This finding suggests that the inactivation can be suppressed, for example, by avoiding use of a base sequence capable of forming a double strand within the base sequence, in the first place. However, this approach ends up limiting the range of applications of the photoresponsive nucleic-acid probe, especially severely when use of a long base sequence is desired.

The inventors of the present invention have conducted further research to avoid this limitation from being imposed on the base sequence of a photoresponsive nucleic-acid probe. Thymine (T), which is a base to which a photoresponsive nucleic acid as a photoresponsive nucleic-acid probe is photo-linked, is known to maintain its ability to undergo photo-crosslinkage with a photoresponsive nucleic acid even when the thymine (T) has various modifications provided that double-strand formation with a complementary strand can still occur. Here, the inventors of the present invention have found that by substituting the C5 of thymine with a cyano group, which is an electron-withdrawing group, and converting the thymine into 5-cyano-2'-deoxyuridine ($^{CN}T$), the speed of photo-crosslinkage with a photoresponsive nucleic acid becomes very low without affecting double-strand formation with a complementary strand. Thus, the present invention has now been completed. In other words, introduction of 5-cyano-2'-deoxyuridine ($^{CN}T$) that is obtained by substituting the C5 of thymine with an electron-withdrawing cyano group can suppress inactivation of a photoresponsive nucleic-acid probe.

In addition to the suppression of inactivation caused by self-crosslinkage occurring within a photoresponsive nucleic-acid probe, the finding described above is also widely applicable to preventing unintended photo-crosslinkage of a thymine (T) or uracil (U) base that is present near a base sequence complementary to a base sequence present near a photoresponsive base, and consequent failure of intended photo-crosslinkage, and also to preventing over-consumption of a photoresponsive nucleic acid and a consequent decrease in efficiency and yield of target reaction.

The present invention subsumes the following, starting from (1).

(1) A method of suppressing photo-crosslinkage of a photoresponsive base having a photo-crosslinkable vinyl structure with a thymine (T) or uracil (U) base that is photo-crosslinkable to the photoresponsive base having a photo-crosslinkable vinyl structure, comprising:
substituting C5 of a pyrimidine ring of the thymine (T) or uracil (U) base with an R group (R is -CN or -CO-$R^1$, and $R^1$ is a saturated or unsaturated, linear or branched, cyclic or acyclic, C1-C12 hydrocarbon group)

(2) The method according to (1), wherein
the photo-crosslinkage is a reaction in which a photo-crosslink is formed between:
the photoresponsive base having a photo-crosslinkable vinyl structure, the photoresponsive base having a photo-crosslinkable vinyl structure being contained in a base sequence of a photoresponsive nucleic acid, and
the thymine (T) or uracil (U) base that is photo-crosslinkable to the photoresponsive base, the thymine (T) or uracil (U) base being contained in a base sequence fraction complementary to a base sequence fraction that is contained in the base sequence of the photoresponsive nucleic acid and is composed of 4 or more bases including the photoresponsive base (the base sequence fraction that is contained in the base sequence of the photoresponsive nucleic acid and is composed of 4 or more bases including the photoresponsive base is called a photoresponsive base sequence fraction) (the base sequence fraction complementary to the photoresponsive base sequence fraction is called a complementary base sequence fraction), and the complementary base sequence fraction being contained in a nucleic acid (a partially-complementary nucleic acid), and
in the complementary base sequence fraction contained in the partially-complementary nucleic acid, at least one constituent nucleotide containing the photo-crosslinkable T or U is replaced by a modified nucleotide of Formula (I):

[chem. 1]

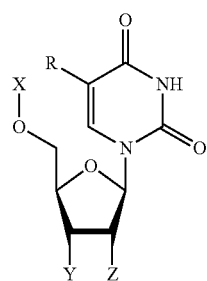

(I)

(in Formula I,
R is -CN or -CO-$R^1$,
$R^1$ is a saturated or unsaturated, linear or branched, cyclic or acyclic, C1-C12 hydrocarbon group, X forms a phosphate group together with O that is bonded to X in Formula I,
Y is a hydroxy group, and
Z is hydrogen or a hydroxy group), the modified nucleotide of Formula (I) being introduced to the complementary base sequence fraction by a phosphodiester bond, and as a result, photo-crosslinkage of the photoresponsive nucleic acid with the partially-complementary nucleic acid is suppressed.

(3) The method according to (1) to (2), wherein
the photoresponsive nucleic acid contains both the photoresponsive base sequence fraction and the complementary base sequence fraction as separate sequence regions within a molecule of the photoresponsive nucleic acid, the molecule of the photoresponsive nucleic acid being the same as a molecule of the partially-complementary nucleic acid, and
suppression of the photo-crosslinkage of the photoresponsive nucleic acid with the partially-complementary nucleic acid is achieved by suppressing self-crosslinkage within the photoresponsive nucleic acid caused by the photo-crosslinkage of the photoresponsive base with the photo-crosslinkable thymine (T) or uracil (U) base.

(4) The method according to any one of (1) to (3), wherein R in Formula (I) is -CN.

(5) The method according to any one of (1) to (4), wherein the photoresponsive base having a photo-crosslinkable vinyl structure is a photoresponsive base having a 3-vinylcarbazole structure.

(6) The method according to any one of (1) to (5), wherein the photoresponsive base having a photo-crosslinkable vinyl structure is a base portion of a modified nucleotide of Formula (II):

[chem. 2]

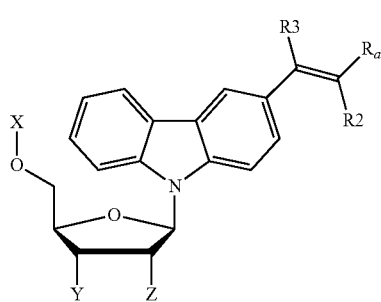

(II)

(in Formula II, $R_a$ is a cyano group, an amido group, a carboxy group, a C2-C7 alkoxycarbonyl group, or hydrogen,
$R_2$ and $R_3$ are independently a cyano group, an amido group, a carboxy group, a C2-C7 alkoxycarbonyl group, or hydrogen,
X forms a phosphate group together with O that is bonded to X in Formula II,
Y is a hydroxy group, and
Z is hydrogen or a hydroxy group), and
the photoresponsive base having a photo-crosslinkable vinyl structure is introduced into the photoresponsive base sequence fraction as a base portion of the modified nucleotide by a phosphodiester bond of the modified nucleotide.

(7) The method according to any one of (1) to (5), wherein the photoresponsive base having a photo-crosslinkable vinyl structure is a base portion of a modified nucleotide of Formula (III):

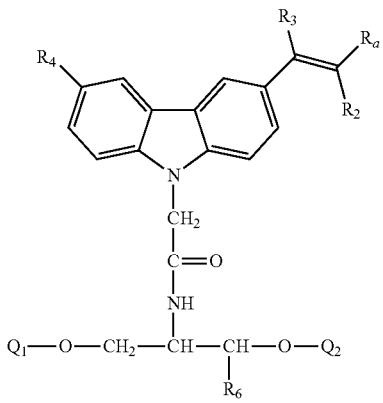

(in Formula III, $R_a$ is a cyano group, an amido group, a carboxy group, a C2-C7 alkoxycarbonyl group, a phosphono group, a sulfo group, or a hydrogen atom, $R_2$ and $R_3$ are independently a cyano group, an amido group, a carboxy group, a C2-C7 alkoxycarbonyl group, or a hydrogen atom, $R_4$ is a hydrogen atom, a hydroxy group, a C1-C3 alkoxy group, a C1-C3 alkylsulfanyl group, a nitro group, a fluorine atom, a fluoromethyl group, a monovalent group of a C6-C12 monocyclic or dicyclic aromatic group, a monovalent group of a monocyclic or dicyclic, C6-C12 heterocyclic aromatic group, or a monovalent group of a formula:

[chem. 3]

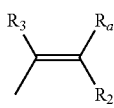

(wherein Ra, $R_2$, and $R_3$ are independent of Ra, $R_2$, and $R_3$ as defined for Formula III and are selected from the groups given above as examples of Ra, $R_2$, and $R_3$ for Formula III), $R_6$ is a hydrogen atom, a methyl group, or an ethyl group, $Q_1$ forms a phosphate group together with O that is bonded to $Q_1$ in Formula III, and $Q_2$ is a hydrogen atom), and the photoresponsive base having a photo-crosslinkable vinyl structure is introduced into the photoresponsive base sequence fraction as a base portion of the modified nucleotide by a phosphodiester bond of the modified nucleotide.

(8) The method according to (7), in which in Formula III, a backbone structure of Formula (IIIa):

[chem. 4]

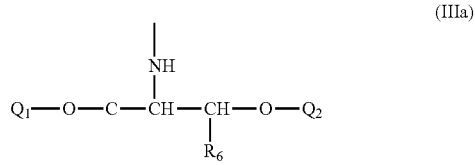

is a D-threoninol structure of the formula:

[chem. 5]

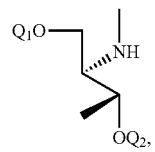

an L-threoninol structure of the formula:

[chem. 6]

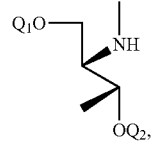

or a serinol structure of the formula:

[chem. 7]

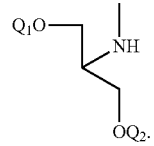

(9) The method according to any one of (1) to (8), wherein every nucleotide containing T or U in the base sequence of the partially-complementary nucleic acid is substituted with the modified nucleotide of Formula (I).

The present invention further subsumes the following, starting from (11).

(11) A photoresponsive nucleic acid with suppressed self-crosslinking ability, comprising:

a photoresponsive base having a photo-crosslinkable vinyl structure, and a modified nucleotide of Formula (I):

[chem. 8]

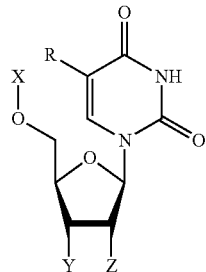
(I)

(in Formula I,

R is -CN or -CO-R$^1$,

R$^1$ is a saturated or unsaturated, linear or branched, cyclic or acyclic, C1-C12 hydrocarbon group, X forms a phosphate group together with O that is bonded to X in Formula I, Y is a hydroxy group, and Z is hydrogen or a hydroxy group), in place of at least one constituent nucleotide containing photo-crosslinkable T or U.

(12) The photoresponsive nucleic acid with suppressed self-crosslinking ability according to (11), wherein R in Formula (I) is -CN.

(13) The photoresponsive nucleic acid with suppressed self-crosslinking ability according to (11) or (12), wherein the photoresponsive base having a photo-crosslinkable vinyl structure is a photoresponsive base having a 3-vinylcarbazole structure.

(14) The photoresponsive nucleic acid with suppressed self-crosslinking ability according to any one of (11) to (13), wherein the photoresponsive base having a photo-crosslinkable vinyl structure is a base portion of a modified nucleotide of Formula (II):

[chem. 9]

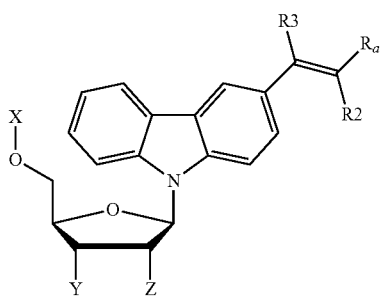
(II)

(in Formula II, R$_a$ is a cyano group, an amido group, a carboxy group, a C2-C7 alkoxycarbonyl group, or hydrogen, R$_2$ and R$_3$ are independently a cyano group, an amido group, a carboxy group, a C2-C7 alkoxycarbonyl group, or hydrogen, X forms a phosphate group together with O that is bonded to X in Formula II, Y is a hydroxy group, and Z is hydrogen or a hydroxy group), and the photoresponsive base having a photo-crosslinkable vinyl structure is introduced into the photoresponsive base sequence fraction as a base portion of the modified nucleotide by a phosphodiester bond of the modified nucleotide.

(15) The photoresponsive nucleic acid with suppressed self-crosslinking ability according to any one of (11) to (13), wherein the photoresponsive base having a photo-crosslinkable vinyl structure is a base portion of a modified nucleotide of or Formula (III):

[chem. 10]

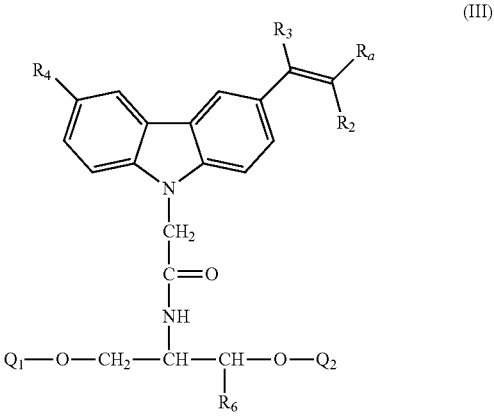
(III)

(in Formula III,

R$_a$ is a cyano group, an amido group, a carboxy group, a C2-C7 alkoxycarbonyl group, a phosphono group, a sulfo group, or a hydrogen atom, R$_2$ and R$_3$ are independently a cyano group, an amido group, a carboxy group, a C2-C7 alkoxycarbonyl group, or a hydrogen atom, R$_4$ is a hydrogen atom, a hydroxy group, a C1-C3 alkoxy group, a C1-C3 alkylsulfanyl group, a nitro group, a fluorine atom, a fluoromethyl group, a monovalent group of a C6-C12 monocyclic or dicyclic aromatic group, a monovalent group of a monocyclic or dicyclic, C6-C12 heterocyclic aromatic group, or a monovalent group of a formula:

[chem. 11]

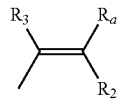

(wherein Ra, R$_2$, and R$_3$ are independent of Ra, R$_2$, and R$_3$ as defined for Formula III and are selected from the groups given above as examples of Ra, R$_2$, and R$_3$ for Formula III), R$_6$ is a hydrogen atom, a methyl group, or an ethyl group, Q$_1$ forms a phosphate group together with O that is bonded to Q$_1$ in Formula III, and Q$_2$ is a hydrogen atom), and the photoresponsive base having a photo-crosslinkable vinyl structure is introduced into the photoresponsive base sequence fraction as a base portion of the modified nucleotide by a phosphodiester bond of the modified nucleotide.
(16) The photoresponsive nucleic acid with suppressed self-crosslinking ability according to (15), in which in Formula III, a backbone structure of Formula (IIIa):

[chem. 12]

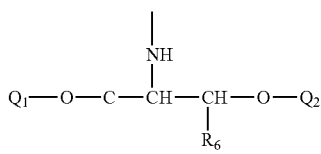
(IIIa)

is a D-threoninol structure of the formula:

[chem. 13]

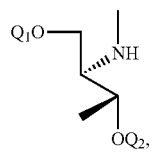

an L-threoninol structure of the formula:

[chem. 14]

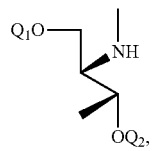

or a serinol structure of the formula:

[chem. 15]

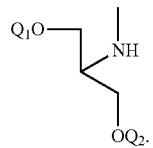

(17) The photoresponsive nucleic acid with suppressed self-crosslinking ability according to any one of (11) to (16), wherein
the photoresponsive nucleic acid with suppressed self-crosslinking ability comprises a base sequence fraction complementary to a base sequence fraction composed of 4 or more bases including the photoresponsive base (the base sequence fraction composed of 4 or more bases including the photoresponsive base is called a photoresponsive base sequence fraction) (the base sequence fraction complementary to the photoresponsive base sequence fraction is called a complementary base sequence fraction), and
the photo-crosslinkable T or U is T or U contained in the complementary base sequence fraction.
(18) The photoresponsive nucleic acid with suppressed self-crosslinking ability according to any one of (11) to (17), wherein every nucleotide containing T or U in the base sequence of the photoresponsive nucleic acid with suppressed self-crosslinking ability is substituted with the modified nucleotide of Formula (I).

Advantageous Effects of Invention

According to the present invention, self-crosslinkage within a photoresponsive nucleic-acid probe used in the photo-clamping method or the like can be suppressed, and as a result, inactivation of the probe can also be prevented. Consequently, the photoresponsive nucleic-acid probe can be enhanced in its reaction efficiency (yield) with no particular limitation given on the type or the length of the base sequence. Furthermore, the present invention can prevent unintended photo-crosslinkage of a thymine (T) or uracil (U) base that is present near a base sequence complementary to a base sequence present near a photoresponsive base, and consequent failure of intended photo-crosslinkage, and can also prevent overconsumption of a photoresponsive nucleic acid and a consequent decrease in efficiency and yield of target reaction. Therefore, the present invention can enhance the range of applications of a photoresponsive nucleic acid.

BRIEF DESCRIPTION OF DRAWINGS

FIG. 4 shows the scheme and the results of photoreaction occurred in an experiment that was carried out to study photo-crosslinkage of a $^{CNV}$K-containing probe.
FIG. 7 is a graph showing the results of an experiment carried out to study photo-crosslinkage of a $^{CNV}$D-containing probe.

DESCRIPTION OF EMBODIMENTS

Figure 1:
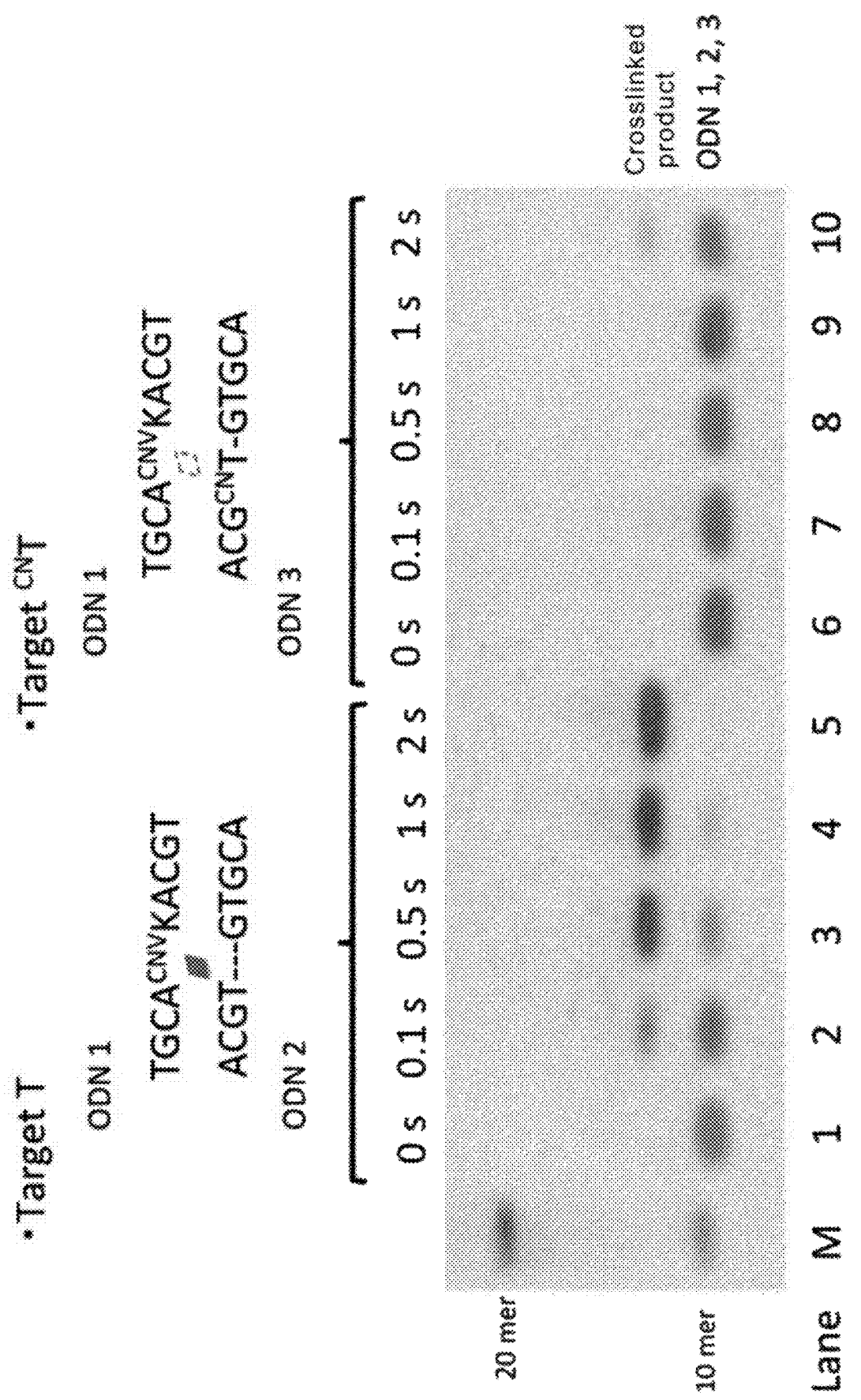
FIG. 1 shows the results of non-native PAGE comparing the photoreactivity of T with the photoreactivity of $^{CN}$T.

In the following, the present invention will be described in detail referring to specific embodiments. The scope of the present invention, however, is not limited to these specific embodiments.

[Photo-Crosslinkage]

A photoresponsive base having a photo-crosslinkable vinyl structure undergoes highly selective photo-crosslinkage with thymine (T) or uracil (U) and cytosine, each of which is a pyrimidine base (Patent Document 1). The photo-crosslinking reaction is a photoreaction, and therefore proceeds extremely rapidly with high efficiency. The desirable solvent conditions and temperature conditions for the photo-crosslinking reaction can be selected from a wide range of conditions including physiological conditions. A photoresponsive base having a 3-vinylcarbazole structure, in particular, undergoes photoreaction, namely, [2+2] photocyclization reaction with a pyrimidine base with high efficiency to form a photo-crosslink.

This photo-crosslinkage also proceeds rapidly and efficiently even when the pyrimidine base has modification. Therefore, suppression of photo-crosslinkage by modifying the pyrimidine base while maintaining complementation necessary for base-pair formation has not been successfully achieved. The photo-crosslinkage also proceeds, for example, when the pyrimidine base is methylcytosine or pseudo uridine.

[Suppression of Photo-Crosslinkage]

Here, according to the present invention, by substituting the C5 of a pyrimidine ring of a thymine (T) or uracil (U) base that is photo-crosslinkable to the photoresponsive base having a photo-crosslinkable vinyl structure, with an R group (R is —CN or —CO—$R^1$, and $R^1$ is a saturated or unsaturated, linear or branched, cyclic or acyclic, C1-C12 hydrocarbon group), photo-crosslinkage can be suppressed while the resulting modified base with substitution does not lose but maintains its complementation necessary for base-pair formation. The suppression of photo-crosslinkage is achieved at an extremely remarkable level, which is indicated by the fact that the efficiency of photo-crosslinking reaction was suppressed to about 1% even under conditions (duration of irradiation) that allowed photo-crosslinking reaction of thymine (T) to proceed at an efficiency of greater than 90% (see the Example section).

[Double-Strand Formation Prior to Photo-Crosslinkage]

Photo-crosslinkage of the photoresponsive base with the thymine (T) or uracil (U) base occurs in the following way: prior to irradiation, a base sequence containing the photoresponsive base together with a base sequence containing the thymine (T) or uracil (U) base form a double strand based on their complementation and are consequently positioned so as to allow photo-crosslinking reaction to occur, and then upon irradiation, photoreaction proceeds well. In a preferred embodiment, a base sequence fraction that is contained in the base sequence of the photoresponsive nucleic acid containing the photoresponsive base and that contains the photoresponsive base (the base sequence fraction is called a photoresponsive base sequence fraction) is complementary to a base sequence fraction containing the thymine (T) or uracil (U) base (the base sequence fraction containing the thymine (T) or uracil (U) base is called a complementary base sequence fraction). In a preferred embodiment, either of the photoresponsive base sequence fraction and the complementary base sequence fraction is stable enough to form a double-stranded region together, and contains at least 4 bases, for example, preferably at least 5 bases, further preferably at least 6 bases, further preferably at least 7 bases, and further preferably at least 8 bases.

[Modified Base and Modified Nucleotide for Photo-Crosslinkage Suppression]

The modified base introduced in place of the photo-crosslinkable thymine (T) or uracil (U) base so as to suppress photo-crosslinkage (the modified base is called a modified base for photo-crosslinkage suppression) has the C5 of the pyrimidine ring substituted with an R group (R is —CN or —CO—$R^1$, and $R^1$ is a saturated or unsaturated, linear or branched, cyclic or acyclic, C1-C12 hydrocarbon group). A modified nucleotide containing the modified base as its base portion (a modified nucleotide for photo-crosslinkage suppression) is a modified nucleotide of Formula (I):

[chem. 16]

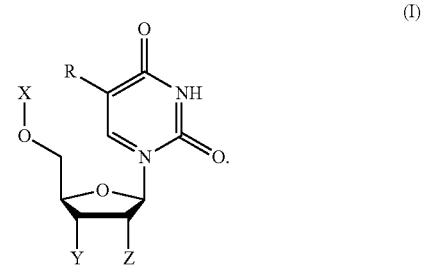

(I)

In Formula I, R is —CN or —CO—$R^1$, preferably —CN (a cyano group). $R^1$ can be any $R^1$ provided that an electron-withdrawing R group is formed, and is a saturated or unsaturated, linear or branched, cyclic or acyclic, C1-C12 hydrocarbon group, for example. Examples of this group include a C1-C3 alkyl group, a cyclohexyl group, a phenyl group, a benzyl group, a tolyl group, and a naphthyl group.

In Formula I, X forms a phosphate group together with O that is bonded to X in Formula I, Y is a hydroxy group, and Z is hydrogen or a hydroxy group.

[Synthesis of Modified Base and Modified Nucleotide for Photo-Crosslinkage Suppression]

The modified base for photo-crosslinkage suppression and the modified nucleotide for photo-crosslinkage suppression can be synthesized by a known means. First, an amidite thereof is synthesized, and then by a known means using a DNA synthesizer or the like, a nucleic acid to which the modified base for photo-crosslinkage suppression is introduced in place of the photo-crosslinkable thymine (T) or uracil (U) base (the nucleic acid is called a modified nucleic acid) can be produced. When desired, the nucleic acid to which the modified base for photo-crosslinkage suppression is introduced in place of the photo-crosslinkable thymine (T) or uracil (U) base (modified nucleic acid) can be produced by first producing a nucleic acid containing the thymine (T) or uracil (U) base or another modified base (modified nucleic acid) and then subjecting the resultant to modification reaction to convert the base into the modified base for photo-crosslinkage suppression.

[Photoresponsive base having photo-crosslinkable vinyl structure]

The photoresponsive base having a photo-crosslinkable vinyl structure is preferably a photoresponsive base having a 3-vinylcarbazole structure, and further preferably a base portion of a modified nucleotide of Formula (II):

[chem. 17]

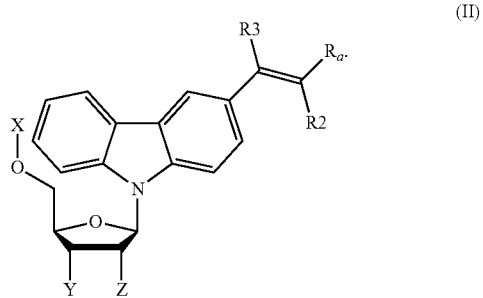

(II)

In Formula II, Ra is a cyano group, an amido group, a carboxy group, a C2-C7 alkoxycarbonyl group, or hydrogen, R2 and R3 are independently a cyano group, an amido group, a carboxy group, a C2-C7 alkoxycarbonyl group, or hydrogen, X forms a phosphate group together with O that is bonded to X in Formula II, Y is a hydroxy group, and Z is hydrogen or a hydroxy group.

In a preferred embodiment, Ra in Formula II is a cyano group, an amido group, a carboxy group, an alkoxycarbonyl group, or hydrogen, preferably a cyano group, an amido group, a carboxy group, an alkoxycarbonyl group, or hydrogen, and further preferably a cyano group, an amido group, a carboxy group, or an alkoxycarbonyl group. The alkoxycarbonyl group that can be used is preferably a C2-C7 alkoxycarbonyl group, further preferably a C2-C6 alkoxycarbonyl group, further preferably a C2-C5 alkoxycarbonyl group, further preferably a C2-C4 alkoxycarbonyl group, further preferably a C2-C3 alkoxycarbonyl group, and particularly preferably a C2 alkoxycarbonyl group.

In a preferred embodiment, R2 and R3 in Formula II are independently a cyano group, an amido group, a carboxy group, an alkoxycarbonyl group, or hydrogen, preferably a cyano group, an amido group, a carboxy group, an alkoxycarbonyl group, or hydrogen, and further preferably a cyano group, an amido group, a carboxy group, or an alkoxycarbonyl group. The alkoxycarbonyl group that can be used is preferably a C2-C7 alkoxycarbonyl group, further preferably a C2-C6 alkoxycarbonyl group, further preferably a C2-C5 alkoxycarbonyl group, further preferably a C2-C4 alkoxycarbonyl group, further preferably a C2-C3 alkoxycarbonyl group, and particularly preferably a C2 alkoxycarbonyl group.

In a preferred embodiment of the present invention, the photoresponsive base having a photo-crosslinkable vinyl structure is a base portion of a modified nucleotide of Formula (III):

[chem. 18]

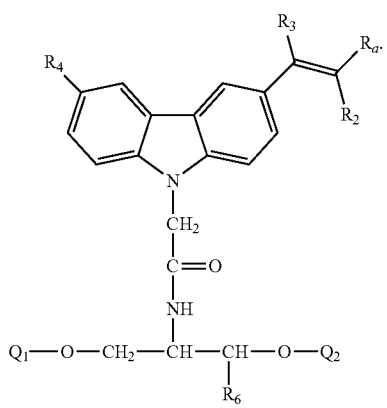

(III)

In Formula III,

Ra is a cyano group, an amido group, a carboxy group, a C2-C7 alkoxycarbonyl group, a phosphono group, a sulfo group, or a hydrogen atom, R2 and R3 are independently a cyano group, an amido group, a carboxy group, a C2-C7 alkoxycarbonyl group, or a hydrogen atom, R4 is a hydrogen atom, a hydroxy group, a C1-C3 alkoxy group, a C1-C3 alkylsulfanyl group, a nitro group, a fluorine atom, a fluoromethyl group, a monovalent group of a C6-C12 monocyclic or dicyclic aromatic compound, a monovalent group of a monocyclic or dicyclic, C6-C12 heterocyclic aromatic compound, or a monovalent group of a formula:

[chem. 19]

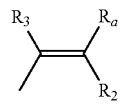

(wherein Ra, R2, and R3 are independent of Ra, R2, and R3 as defined for Formula III, and are selected from the groups given above as examples of Ra, R2, and R3 for Formula III), R6 is a hydrogen atom, a methyl group, or an ethyl group, $Q_1$ forms a phosphate group together with O that is bonded to $Q_1$ in Formula III, and $Q_2$ is a hydrogen atom.

Ra, R2, and R3 in Formula III can be independently the same as Ra, R2, and R3 as defined for Formula II.

For example, R4 in Formula III can be selected from the following groups (each wavy line indicates where the free valency is located).

[chem. 20]

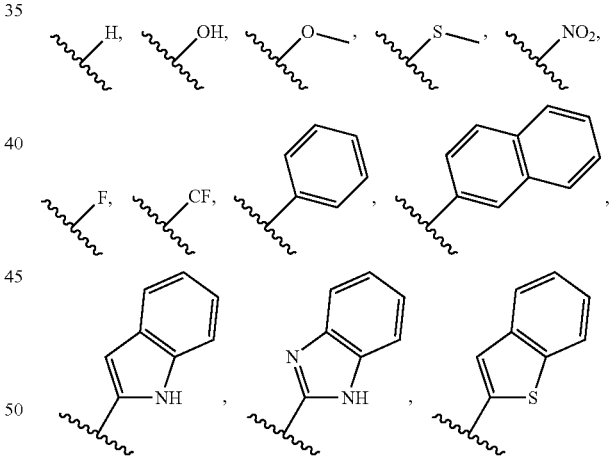

In a preferred embodiment, in Formula III, the backbone structure of Formula (IIIa):

[chem. 21]

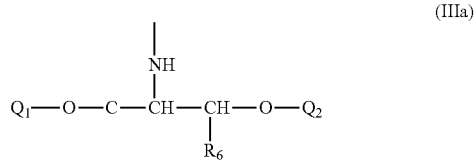

(IIIa)

is a D-threoninol structure of a formula:

[chem. 22]

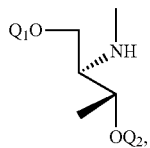

an L-threoninol structure of a formula:

[chem. 23]

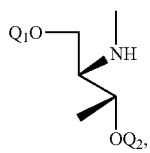

or a serinol structure of a formula:

[chem. 24]

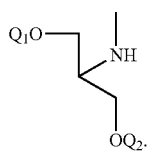

The sugar backbone portion of the modified nucleotide of Formula III is not of a ribose (or deoxyribose) structure as in a natural nucleotide or the modified nucleotide of Formula II, but is replaced by the backbone structure of Formula IIIa. Therefore, the modified nucleotide of Formula III can also be called an artificial photoresponsive nucleotide analog. Even though it has such a different backbone structure, the modified nucleotide of Formula III unexpectedly acts as a photoresponsive base as far as its incorporation into a nucleic acid and its photoresponsivity are concerned. Based on this finding, the inventors of the present invention have already filed a patent application in Japan (Japanese Patent Application No. 2013-70381).

[Suppression of Self-Crosslinkage]

The suppression of photo-crosslinkage according to the present invention is useful, needless to say, when the photoresponsive base and the thymine (T) or uracil (U) base are contained in separate nucleic acid molecules and the photo-crosslinkage occurs between these separate nucleic acid molecules. The suppression of photo-crosslinkage according to the present invention is also useful, in particular, when the photoresponsive base and the thymine (T) or uracil (U) base are contained in the same nucleic acid molecule and self-crosslinkage occurs within the nucleic acid molecule. For example, a photoresponsive nucleic-acid probe used in the photo-clamping method can have a double-stranded section formed within the nucleic acid molecule, depending on the base sequence of the nucleic acid molecule. In this case, when the double-stranded section contains both a photoresponsive base and a thymine (T) or uracil (U) base positioned in a way that they can undergo photo-crosslinkage, the photoresponsive nucleic-acid probe undergoes intramolecular self-crosslinkage and consequently fails to participate in intended photo-crosslinking reaction, resulting in a significant decrease in the efficiency of use of the probe (or in the yield). By suppressing self-crosslinkage within the photoresponsive nucleic-acid probe, loss of the probe is prevented and excellent efficiency of use (or high yield) is obtained. In other words, in a preferred embodiment, the photoresponsive base sequence fraction and the complementary base sequence fraction are contained in the same nucleic acid molecule and self-crosslinkage therebetween is suppressed.

[Substitution of Every Thymine (T) or Uracil (U) Base]

According to the present invention, by substituting at least one photo-crosslinkable thymine (T) or uracil (U) base in the nucleic acid molecule with the modified base for photo-crosslinkage suppression, photo-crosslinkage of the thymine (T) or uracil (U) base can be suppressed. Therefore, substitution of at least one base is subsumed within the scope of the present invention.

The nucleic acid substituted with the modified base for photo-crosslinkage suppression of the present invention is superior to an unsubstituted nucleic acid containing a thymine (T) or uracil (U) base because the Tm value thereof does not fluctuate and the ability thereof to form a double strand is maintained. In other words, substitution with the modified base for photo-crosslinkage suppression of the present invention does not affect the ability thereof to form a double strand, and therefore there is no need to limit the number of substitution to the minimum and instead every thymine (T) or uracil (U) base contained in a target nucleic acid molecule can be substituted with the modified base for photo-crosslinkage suppression. Substitution of every thymine (T) or uracil (U) base is advantageous because no analysis is required on the structure of the complementary strand and substitution can be carried out uniformly across the complementary strand to suppress any undesired photo-crosslinkage. Substitution of every thymine (T) or uracil (U) base is particularly advantageous, for example, when producing photoresponsive nucleic-acid probes having many different base sequences.

[Reaction Conditions in Photo-Crosslinkage Suppression]

According to the present invention, photo-crosslinkage can be suppressed under conventionally known conditions for photo-crosslinkage. For example, the light for irradiation to cause photo-crosslinkage usually has a wavelength within the range from 350 nm to 380 nm, preferably has a wavelength within the range from 360 nm to 370 nm, further preferably has a wavelength of 366 nm, and particularly preferably is laser light having a single wavelength of 366 nm. The suppression of photo-crosslinkage can be achieved under any of these irradiation conditions.

EXAMPLES

The present invention will be described in detail referring to examples. The scope of the present invention, however, is not limited to these examples.

[Synthesis of $^{CNV}$K-Containing ODN]

Synthesis of an amidite of a nucleotide ($^{CNV}$K) of a formula:

[chem. 25]

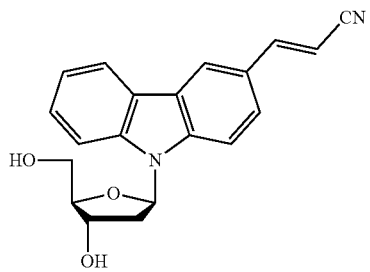

3-cyanovinylcarbazole ($^{CNV}$K)

was carried out according to Scheme 1 below. Synthesis was carried out according to the procedure disclosed in Patent Document 1 (International Publication No. WO 2009/066447).

Scheme 1

[chem. 26]

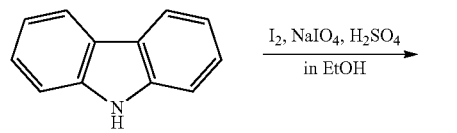

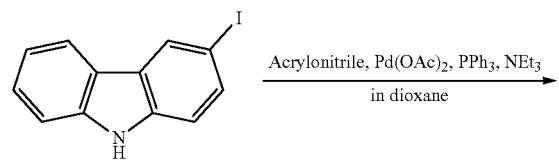

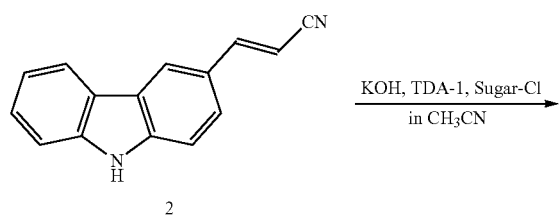

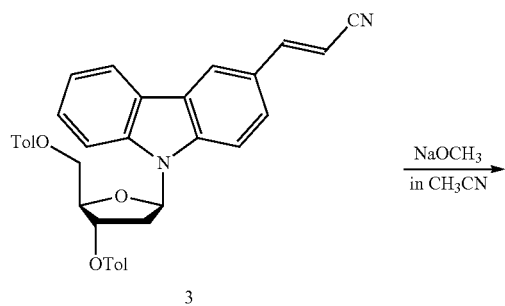

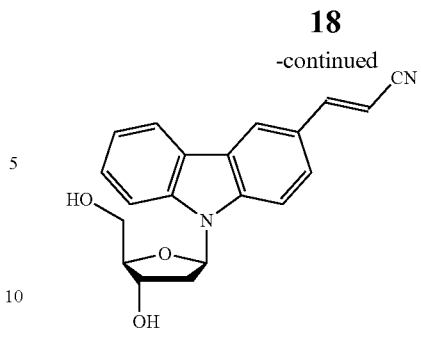

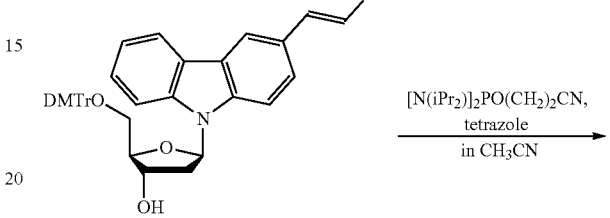

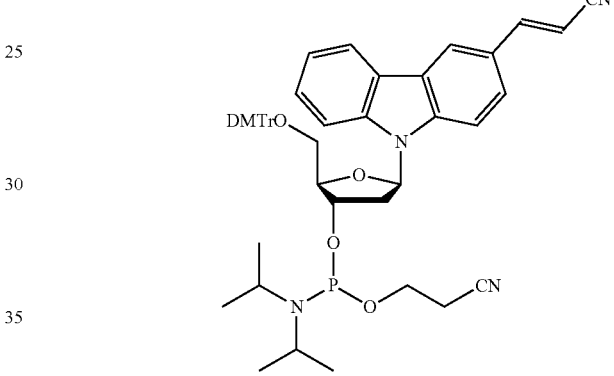

In the same manner, an amidite of a nucleotide ($^{CN}$T) of a formula:

[chem. 27]

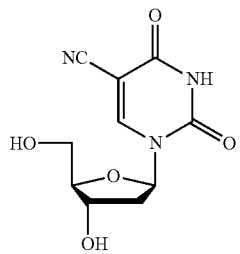

5-cyano-2'-deoxyuridine ($^{CN}$T)

was synthesized.

The resulting amidites of the artificial photoresponsive nucleic acids, namely, 3-cyanovinylcarbazole nucleotide ($^{CNV}$K) and 5-cyano-2'-deoxyuridine ($^{CN}$T) were made to be 100 mM with the use of acetonitrile, and an ABI3400 was used to synthesize an ODN. The sequence of the resulting ODN is shown in Table 1. Following synthesis, deprotection was carried out with a 28% aqueous ammonia solution at 55° C. for 8 hours. Subsequently, purification was carried out with HPLC, followed by mass spectroscopy, which confirmed that the intended sequence was obtained.

TABLE 1

ODNs used in experiment

| | Sequence (5'-3') | | Number of bases |
|---|---|---|---|
| ODN 1 | TGCA$^{CNV}$KACGT | (SEQ ID NO: 4) | 9 |
| ODN 2 | ACGTGTGCA | (SEQ ID NO: 5) | 9 |
| ODN 3 | ACGTG$^{CN}$TGCA | (SEQ ID NO: 6) | 9 |
| ODN 4 | GTA$^{CNV}$KAGAGTGTA | (SEQ ID NO: 1) | 13 |
| ODN 5 | G$^{CN}$TA$^{CNV}$KAGAG$^{CN}$TG$^{CN}$TA | (SEQ ID NO: 2) | 13 |
| ODN 6 | AGAGTACACTCTATACTGAG | (SEQ ID NO: 3) | 20 |

[Analysis of Photoreactivity of $^{CNV}$K and $^{CN}$T]

A buffer (100 mM NaCl, 50 mM sodium cacodylate) containing 20 μM of ODN1 and 20 μM of ODN2 or 20 μM of ODN3 was heated at 90° C. for 5 minutes, followed by annealing with the temperature being slowly lowered to 4° C. Subsequently, a UV-LED irradiator was used to perform irradiation of UV at 366 nm at 4° C., and non-native PAGE analysis was carried out to confirm that a photo-crosslinked product had been formed by irradiation. The results are shown in FIG. 1.

FIG. 1 shows the results of non-native PAGE comparing the photoreactivity of T with the photoreactivity of $^{CN}$T. As for the lanes in FIG. 1, M: 10 DNA Ladder Maker, Lanes 1 to 5: T as Target base, Lanes 6 to 10: $^{CN}$T as Target base. Duration of irradiation was 0 s (second), 0.1 s, 0.5 s, 1 s, and 2 s. ODN1 and ODN2 hybridized with each other to form a double strand, and upon irradiation, $^{CNV}$K underwent photo-crosslinkage with a photoresponsive base (Target base) T facing and complementary to the base adjacent to $^{CNV}$K on the 5' side. Electrophoresis detected a crosslinked product. The sequence of ODN1 and the sequence of ODN3 also hybridized with each other to form a double strand, and in this case, the base (Target base) facing and complementary to the base adjacent to $^{CNV}$K on the 5' side was $^{CN}$T.

When ODN1 and ODN2 were paired, in other words, when the Target base was T, irradiation for 2 seconds resulted in near disappearance of a band attributable to the starting molecule, 9 mer. When ODN1 and ODN3 were paired, in other words, when Target was $^{CN}$T, no band attributable to a crosslinked product was confirmed even after irradiation for 2 seconds. These results have proven that reactivity is significantly different between when the base to which $^{CNV}$K crosslinked to is T and when the base to which $^{CNV}$K crosslinked to is $^{CN}$T. In order to investigate whether crosslinking reaction does not proceed at all or proceeds slowly when the base to which $^{CNV}$K crosslinked to is $^{CN}$T, another non-native PAGE analysis was carried out on samples that had undergone longer irradiation. The results are shown in FIG. 2.

Figure 2:
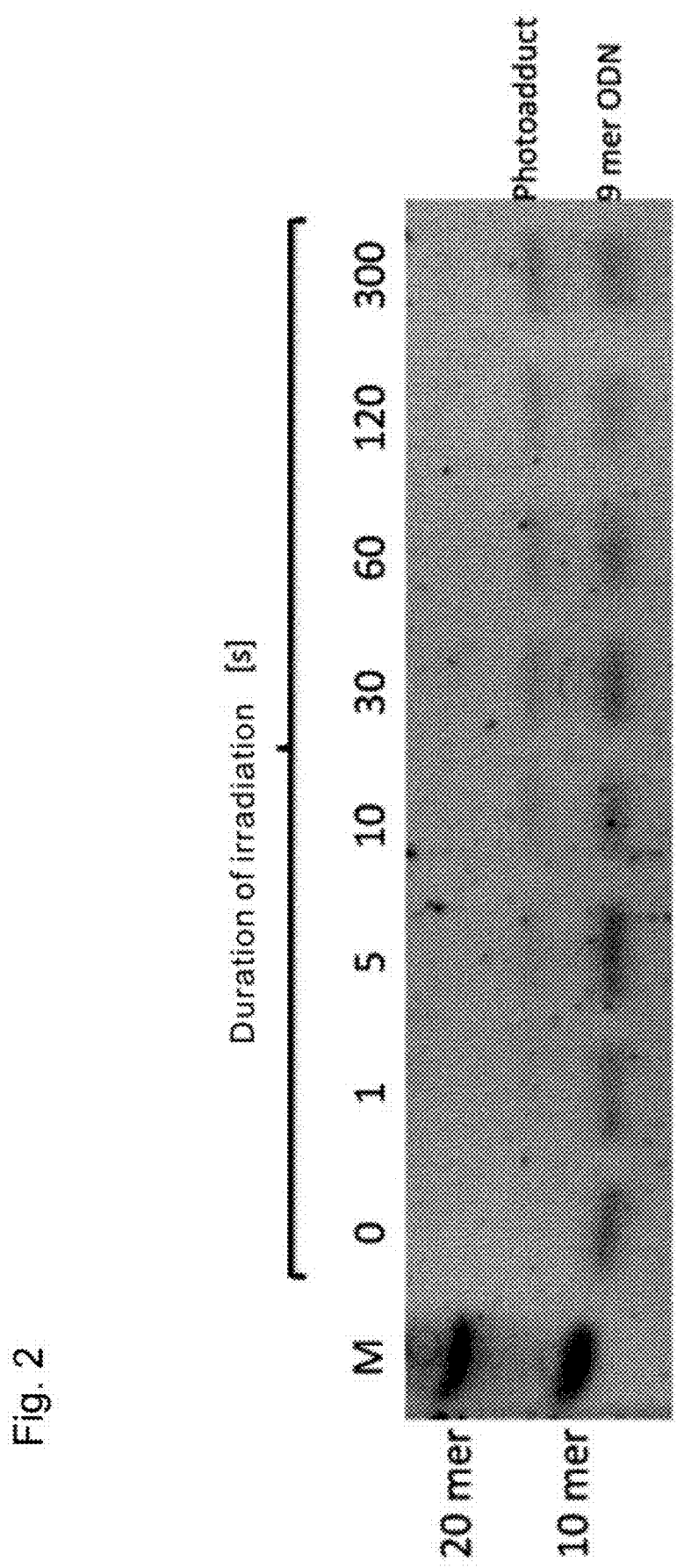
FIG. 2 shows the results of non-native PAGE analysis on samples that underwent longer irradiation.

FIG. 2 shows the results of non-native PAGE analysis of samples that underwent longer irradiation. As for the lanes, the lane M is attributed to 10 bp DNA Ladder Maker, and the rest are attributed to duration of irradiation of 0 second, 1 second, 5 seconds, 10 seconds, 30 seconds, 60 seconds, 120 seconds, and 300 seconds.

FIG. 2 shows that when ODN1 and ODN3 were paired, bands probably attributable to a photo-crosslinked product were barely confirmed for samples that had been irradiated for significantly extended periods of time. These results have proven that $^{CN}$T in which the C5 of thymine is substituted with a cyano group is crosslinked to $^{CNV}$K at a speed much lower than thymine (T) is.

For quantitative discussion, HPLC analysis was carried out and the decrement of ODN3 was used to calculate a photo-crosslinking rate. The results are shown in FIG. 3.

Figure 3:
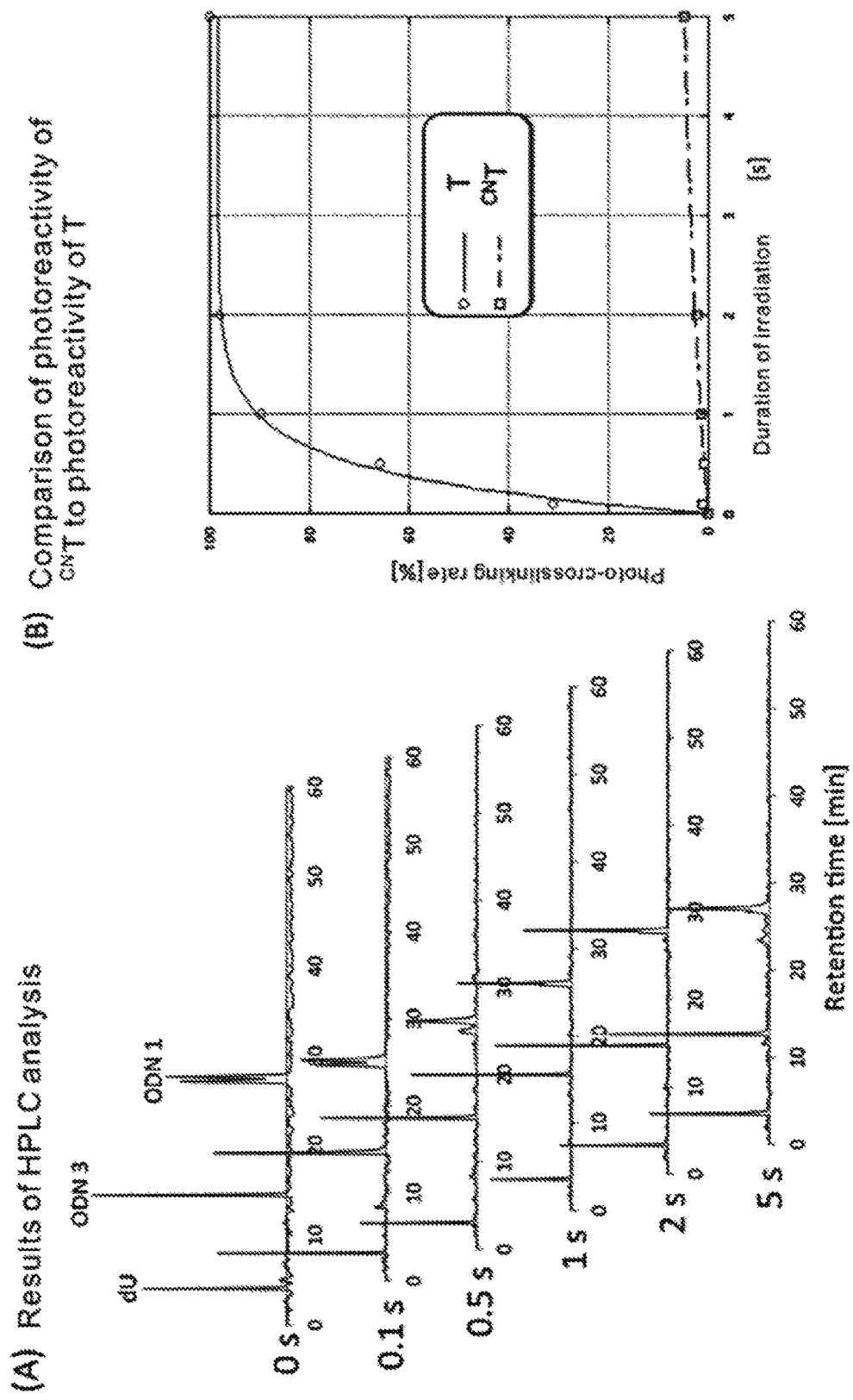
FIG. 3 shows HPLC charts and a graph showing the difference in photoreactivity between $^{CN}$T and T.

FIG. 3 includes FIG. 3(A), which shows the results of HPLC analysis regarding crosslinking reaction between ODN1 and ODN3. FIG. 3(A) shows charts obtained after irradiation for 0 s (second), 0.1 s, 0.5 s, 1 s, 2 s, and 5 s, with the abscissa indicating retention time (minute). FIG. 3 also includes FIG. 3(B), which is a graph comparing the photoreactivity of ODN2 (T) with the photoreactivity of ODN3 ($^{CN}$T). The abscissa indicates duration of irradiation (second), and the ordinate indicates the photo-crosslinking rate (%). In FIG. 3(B), the upper approximate curve is drawn for ODN2 (T), and the lower approximate curve is drawn for ODN3 ($^{CN}$T).

These HPLC results have also proven that mere several seconds of irradiation allowed almost no photo-crosslinking reaction to proceed between $^{CN}$T and $^{CNV}$K. The photo-crosslinking rate calculated from the decrement of ODN3 occurred upon irradiation was about 1% when Target was $^{CN}$T and the duration of irradiation was 1 second, compared to 90% or higher when Target was T and the duration of irradiation was 1 second. Curve fitting was carried out to obtain an approximate curve, which has proven that photo-crosslinking reaction proceeded slowly when Target was $^{CN}$T, at about 1/80 the speed when Target was thymine.

[Suppression of Inactivation of $^{CNV}$K-Containing Probe]

$^{CNV}$K is highly photoresponsive, and therefore may undergo crosslinkage even when the double strand structure is only temporarily formed and not very stable. Formation of a self-crosslinked structure, in particular, is considered to cause inactivation of a $^{CNV}$K-containing probe. Based on the findings above that $^{CN}$T is poorly photoresponsive to $^{CNV}$K, an experiment was carried out to study suppression of inactivation of a $^{CNV}$K-containing probe.

Prior to a series of experiments, screening was first carried out to select a self-crosslinkable base sequence. As a result, determination was made to use the ODN4 sequence, and the experiments followed.

A buffer (100 mM NaCl, 50 mM sodium cacodylate) containing 20 μM of Probe ODN (ODN4 or ODN5) and 20 μM of ODN6 was heated at 90° C. for 5 minutes, followed by annealing with the temperature being slowly lowered to 25° C. As for Lanes 5 and 6, sample preparation was followed by heating at 90° C. for 5 minutes, and then the resultant was immediately transferred to 25° C. for rapid quenching. As for Lanes 7 and 8, Probe ODN at 20 μM and ODN6 at 4 μM were used, where the contents of Probes were 5 times greater than the content of Target. These samples were irradiated with UV at 366 nm with the use of a UV-LED irradiator, at 25° C. for 10 seconds. Then, non-native PAGE analysis was performed. The procedure and the results are shown in FIG. 4.

FIG. 4 shows the scheme and the results of photoreaction occurred in an experiment that was carried out to study photo-crosslinkage of a $^{CNV}$K-containing probe. FIG. 4(A) is a descriptive view of the scheme of photoreaction of the $^{CNV}$K-containing probe undergoing photo-crosslinkage. FIG. 4(B) shows the results of non-native PAGE carried out in the experiments. As for the lanes in FIG. 4(B), Lane M is attributable to 10 bp DNA Ladder Maker, Lanes 1 and 2 are attributable to Probe alone, Lanes 3 and 4 are attributable to Probe and Target, Lanes 5 and 6 are attributable to Probe and Target after rapid quenching, and Lanes 7 and 8 are attributable to the case where the contents of Probes were 5 times greater than the content of Target (5 equivalents). Lanes 2, 4, 6, and 8 received irradiation, and Lanes 1, 3, 5, and 7 received no irradiation.

After irradiation, the $^{CNV}$K-containing probe used here yielded a new band slightly off, to the low-molecular-weight side, the band attributable to the starting molecule. This new band did not appear in the case of no irradiation, appeared when the $^{CNV}$K-containing probe (ODN4) alone was added, and appeared separately from the band attributable to ODN4 when electrophoresis was carried out under non-native conditions. From these and other results, the new band was probably attributable to a self-crosslinked product resulting from intramolecular photo-crosslinkage within the $^{CNV}$K-containing probe (ODN4).

Another experiment was carried out in the same manner but using a probe in which every T contained in ODN4 was substituted with $^{CN}$T. The results are shown in FIG. 5.

Figure 5:
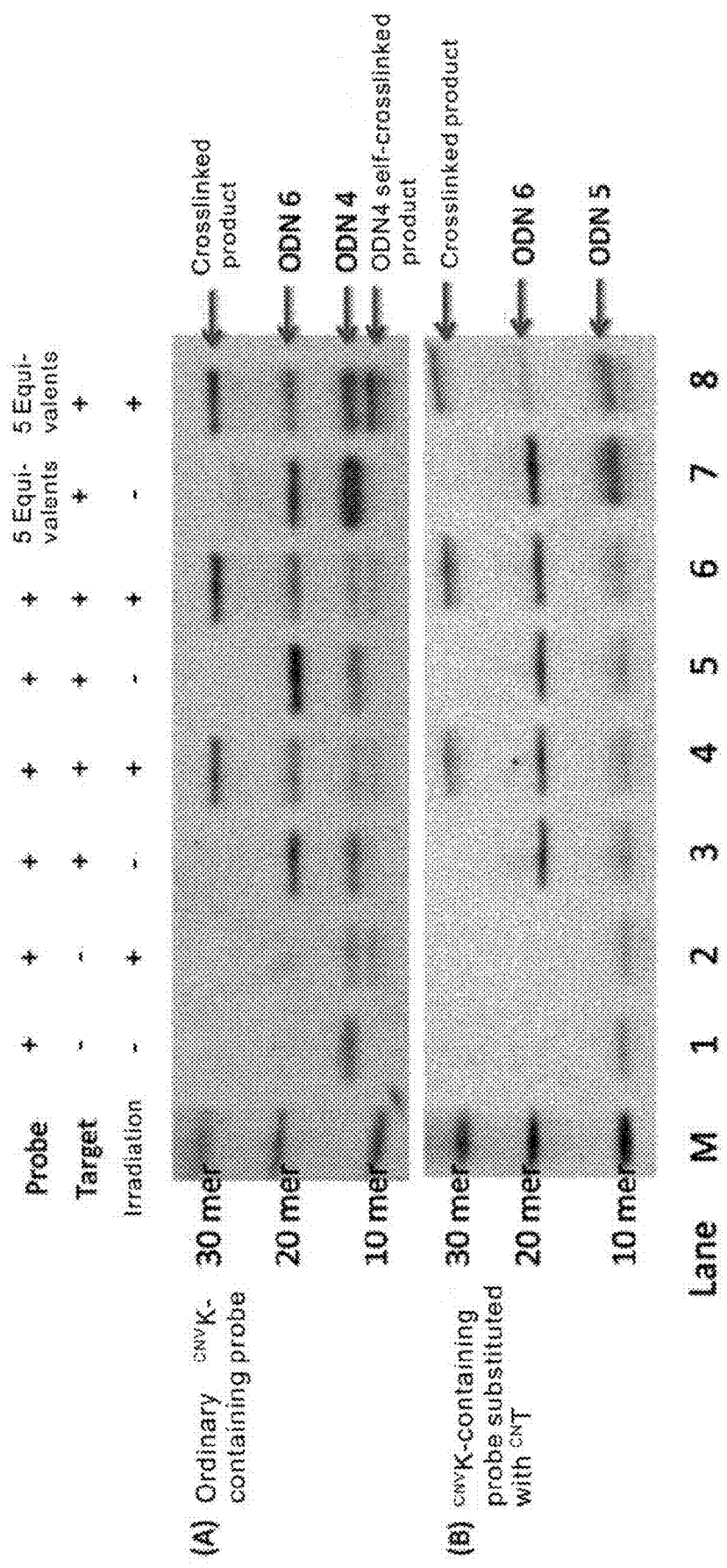
FIG. 5 shows the results of an experiment carried out to study the ability of $^{CN}$T to suppress inactivation of a $^{CNV}$K-containing probe.

FIG. 5 shows the results of an experiment carried out to study suppression of inactivation of a $^{CNV}$K-containing probe by $^{CN}$T. FIG. 5(A) shows the results with an ordinary probe, and FIG. 5(B) shows the results with a probe substituted with $^{CN}$T. As for the lanes, Lane M is attributable to 10 bp DNA Ladder Maker, Lanes 1 and 2 are attributable to Probe alone, Lanes 3 and 4 are attributable to Probe and Target, Lanes 5 and 6 are attributable to Probe and Target after rapid quenching, and Lanes 7 and 8 are attributable to the case where the contents of Probes were 5 times greater than the content of Target (5 equivalents). Lanes 2, 4, 6, and 8 received irradiation, and Lanes 1, 3, 5, and 7 received no irradiation.

As shown in the results, substitution of T in the $^{CNV}$K-containing probe (ODN4) with $^{CN}$T resulted in no band confirmed attributable to a self-crosslinked product and a band noticeably appeared attributable to a crosslinked product. Thus, by substituting T contained in the $^{CNV}$K-containing probe with $^{CN}$T, only the self-crosslinkage within the $^{CNV}$K-containing probe (ODN5) can be suppressed with no inhibition occurring on double-strand formation or on photo-crosslinking reaction with ODN6 targeted by the $^{CNV}$K-containing probe, and, as a result, inactivation of the probe can be suppressed.

Within the $^{CNV}$K-containing probe, base sequence sections that are self-crosslinkable are very limited. However, in such a case that various sequences present in living organisms are targeted or a long-chain probe is used, undesired self-crosslinkage can occur. By substituting T contained in the $^{CNV}$K-containing probe with $^{CN}$T as described above, such undesired self-crosslinkage can be suppressed. Substitution of T with $^{CN}$T does not impair the ability of the probe to form a double strand and to undergo photo-crosslinking reaction, and therefore every T can be substituted with $^{CN}$T. For example, simulation can be carried out to predict a structure that is self-crosslinkable to a certain extent, and then only the Ts contained in the structure predicted to be self-crosslinkable can be substituted with $^{CN}$Ts. These findings allow a $^{CNV}$K-containing probe to be used in a wider range of applications and to be applied to a wider range of sequences.

[Tm Value]

Between the Tm value for the pair of ODN1 and ODN2 and the Tm value for the pair of ODN1 and ODN3, no measurable difference was observed. This indicates that the ability to form a double strand was maintained after substitution of T with $^{CN}$T.

[Synthesis of $^{CNV}$D-Containing ODN]

A nucleotide analog ($^{CNV}$D) of the following formula was synthesized according to Scheme 2. Subsequently, an amidite of the nucleotide analog ($^{CNV}$D) was synthesized, which was then used to synthesize ODN in the same manner as in the case of $^{CNV}$K above, for use in analysis of photoreactivity with $^{CN}$T.

[chem. 28]

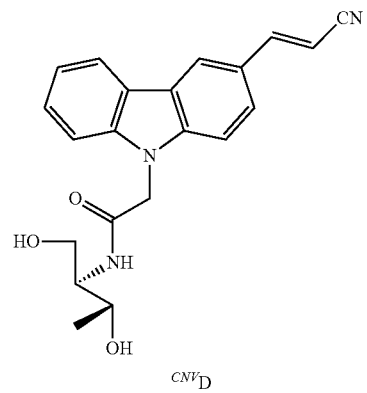

$^{CNV}$D (Scheme 2)

[chem. 29]

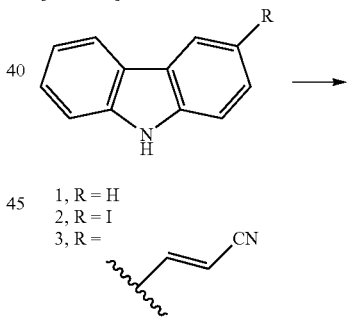

1, R = H
2, R = I
3, R =

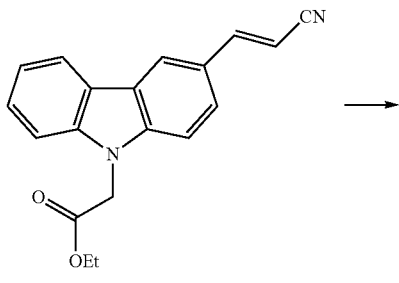

4

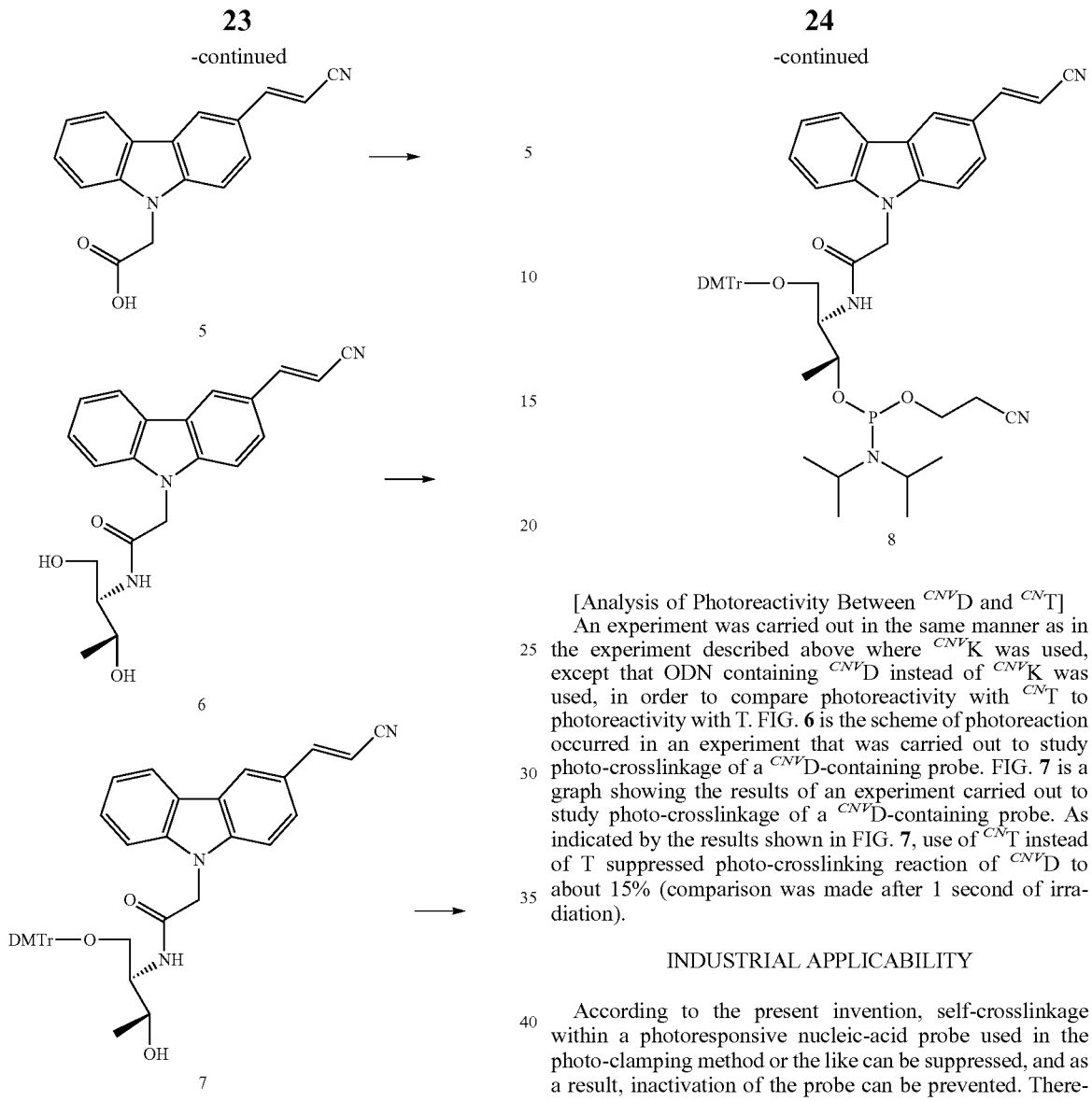

[Analysis of Photoreactivity Between $^{CNV}$D and $^{CN}$T]

Figure 6:
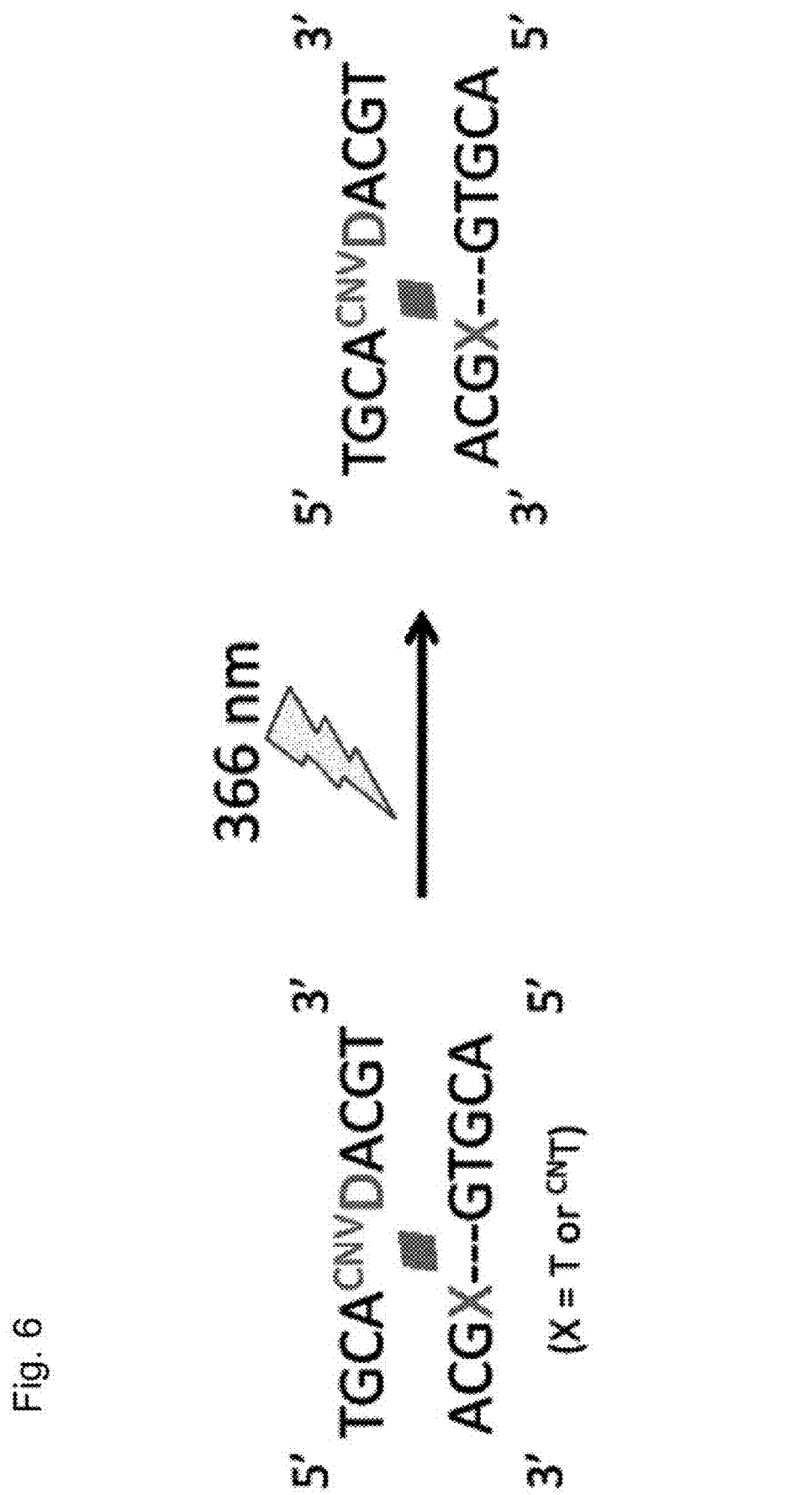
FIG. 6 is the scheme of photoreaction occurred in an experiment that was carried out to study photo-crosslinkage of a $^{CNV}$D-containing probe.

An experiment was carried out in the same manner as in the experiment described above where $^{CNV}$K was used, except that ODN containing $^{CNV}$D instead of $^{CNV}$K was used, in order to compare photoreactivity with $^{CN}$T to photoreactivity with T. FIG. 6 is the scheme of photoreaction occurred in an experiment that was carried out to study photo-crosslinkage of a $^{CNV}$D-containing probe. FIG. 7 is a graph showing the results of an experiment carried out to study photo-crosslinkage of a $^{CNV}$D-containing probe. As indicated by the results shown in FIG. 7, use of $^{CN}$T instead of T suppressed photo-crosslinking reaction of $^{CNV}$D to about 15% (comparison was made after 1 second of irradiation).

INDUSTRIAL APPLICABILITY

According to the present invention, self-crosslinkage within a photoresponsive nucleic-acid probe used in the photo-clamping method or the like can be suppressed, and as a result, inactivation of the probe can be prevented. Therefore, the present invention is industrially useful.

The invention claimed is:

1. A double stranded nucleic acid, comprising:
a first oligonucleotide, the first oligonucleotide comprising a modified nucleotide having a structure corresponding to the monomer of Formula (II) or an amino acid analogue of a nucleotide having a structure corresponding to the monomer of Formula (III):

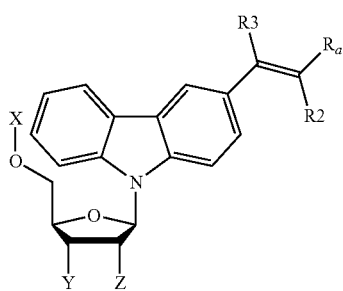

(II)

wherein, in Formula II,
$R_a$ is a cyano group, a carboxy group, a C2-C7 alkoxycarbonyl group, or a hydrogen atom,
$R_2$ and $R_3$ are independently a cyano group, a carboxy group, a C2-C7 alkoxycarbonyl group, or a hydrogen atom,
X forms a phosphate group together with O that is bonded to X,
Y is a hydroxy group, and
Z is a hydrogen atom or a hydroxyl group;

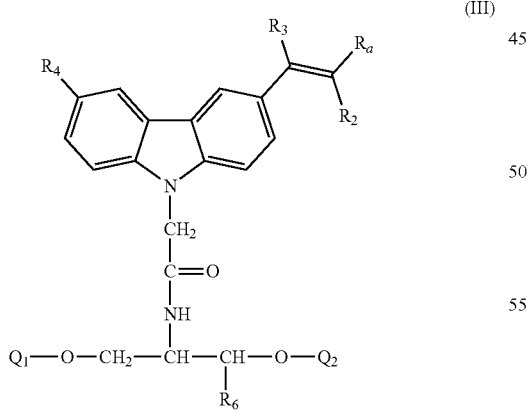

(III)

wherein, in Formula III,
$R_a$ is a cyano group, a carboxy group, a C2-C7 alkoxycarbonyl group, a phosphono group, a sulfo group, or a hydrogen atom,
$R_2$ and $R_3$ are independently a cyano group, a carboxy group, a C2-C7 alkoxycarbonyl group, or a hydrogen atom, $R_4$ is a hydrogen atom, a hydroxy group, a C1-C3 alkoxy group, a C1-C3 alkylsulfanyl group, a nitro group, a fluorine atom, a fluoromethyl group, a monovalent group of a C6-C12 monocyclic or dicyclic aromatic group, a naphthyl group, an indolyl group, a benzoimidazolyl group, a benzothiophenyl group, or a monovalent group of a formula:

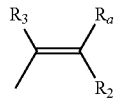

wherein $R_a$, $R_2$, and $R_3$ are independent of $R_a$, $R_2$, and $R_3$ as defined for Formula III and are selected from the groups given above as examples of $R_a$, $R_2$, and $R_3$ for Formula III,
$R_6$ is a hydrogen atom, a methyl group, or an ethyl group,
$Q_1$ forms a phosphate group together with O that is bonded to $Q_1$, and
$Q_2$ is a hydrogen atom, and
wherein the modified nucleotide having the structure corresponding to the monomer of Formula (II) or the amino acid analogue of the nucleotide having the structure corresponding to the monomer of Formula (III) is introduced into a base sequence fraction as a base portion of the modified nucleotide having the structure corresponding to the monomer of Formula (II) or the amino acid analogue of the nucleotide having the structure corresponding to the monomer of Formula (III) by a phosphodiester bond, and
a second oligonucleotide, the second oligonucleotide comprising a modified nucleotide having a structure corresponding to the monomer of Formula (I):

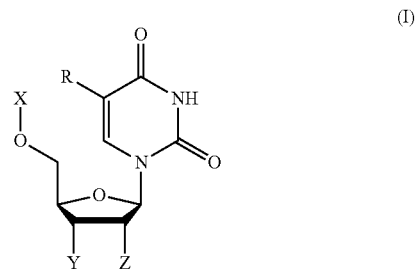

(I)

wherein, in Formula I:
R is -CN or -CO-$R^1$,
$R^1$ is a saturated or unsaturated, linear or branched, cyclic or acyclic, C1-C12 hydrocarbon group,
X forms a phosphate group together with O that is bonded to X,
Y is a hydroxy group, and
Z is a hydrogen atom or a hydroxy group, and
wherein the first oligonucleotide and the second oligonucleotide are hybridized.

2. The double stranded nucleic acid according to claim 1, wherein R in Formula (I) is a cyano group.

3. The double stranded nucleic acid according to claim 2, wherein the first oligonucleotide comprises 4 or more bases.

4. The double stranded nucleic acid according to claim 1, wherein the first oligonucleotide comprises 4 or more bases.

5. The double stranded nucleic acid according to claim 4, wherein the modified nucleotide having the structure corresponding to the monomer of Formula (I) in the second oligonucleotide is at every position complementary to the modified nucleotide having the structure corresponding to the monomer of Formula (II) or the amino acid analogue of the nucleotide having the structure corresponding to the monomer of Formula (III) in the first oligonucleotide.

6. The double stranded nucleic acid according to claim 1, wherein the first oligonucleotide contains the modified nucleotide having the structure corresponding to the monomer of Formula (I), and
wherein the modified nucleotide having the structure corresponding to the monomer of Formula (I) replaces at least one constituent nucleotide which is the photo-crosslinkable thymine (T) or uracil (U).

7. The double stranded nucleic acid according to claim 6, wherein R in Formula (I) is a cyano group.

8. The double stranded nucleic acid according to claim 7, wherein the first oligonucleotide comprises 4 or more bases.

9. The double stranded nucleic acid according to claim 6, wherein, in Formula (I), R is a cyano group, and Z is a hydrogen atom.

10. The double stranded nucleic acid according to claim 9, wherein the first oligonucleotide comprises 4 or more bases.

11. The double stranded nucleic acid according to claim 6, wherein either:
  1) in Formula (II), $R_a$ is a cyano group, $R_2$ and $R_3$ are hydrogen atoms, and Z is a hydrogen atom, or
  2) in Formula (III), $R_a$ is a cyano group, $R_2$, $R_3$ and $R_4$ are hydrogen atoms, $R_6$ is a methyl group, and $Q_2$ is a hydrogen atom.

12. The double stranded nucleic acid according to claim 11, wherein the first oligonucleotide comprises 4 or more bases.

13. The double stranded nucleic acid according to claim 6, wherein, in Formula (I), R is a cyano group, and Z is a hydrogen atom, and
wherein either:
  1) in Formula (II), $R_a$ is a cyano group, $R_2$ and $R_3$ are hydrogen atoms, and Z is a hydrogen atom, or
  2) in Formula (III), $R_a$ is a cyano group, $R_2$, $R_3$ and $R_4$ are hydrogen atoms, $R_6$ is a methyl group, and $Q_2$ is a hydrogen atom.

14. The double stranded nucleic acid according to claim 13, wherein the first oligonucleotide comprises 4 or more bases.

15. The double stranded nucleic acid according to claim 1, wherein, in Formula (I), R is a cyano group, and Z is a hydrogen atom.

16. The double stranded nucleic acid according to claim 15, wherein the first oligonucleotide comprises 4 or more bases.

17. The double stranded nucleic acid according to claim 1, wherein either:
  1) in Formula (II), $R_a$ is a cyano group, $R_2$ and $R_3$ are hydrogen atoms, and Z is a hydrogen atom, or
  2) in Formula (III), $R_a$ is a cyano group, $R_2$, $R_3$ and $R_4$ are hydrogen atoms, $R_6$ is a methyl group, and $Q_2$ is a hydrogen atom.

18. The double stranded nucleic acid according to claim 17, wherein the first oligonucleotide comprises 4 or more bases.

19. The double stranded nucleic acid according to claim 1, wherein, in Formula (I), R is a cyano group, and Z is a hydrogen atom, and
wherein either:
  1) in Formula (II), $R_a$ is a cyano group, $R_2$ and $R_3$ are hydrogen atoms, and Z is a hydrogen atom, or
  2) in Formula (III), $R_a$ is a cyano group, $R_2$, $R_3$ and $R_4$ are hydrogen atoms, $R_6$ is a methyl group, and $Q_2$ is a hydrogen atom.

20. The double stranded nucleic acid according to claim 19, wherein the first oligonucleotide comprises 4 or more bases.

21. A single stranded oligonucleotide comprising a modified nucleotide having a structure corresponding to the monomer of Formula (I):

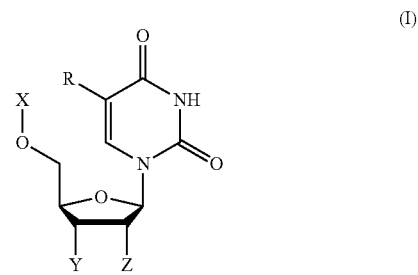

wherein, in Formula I:
R is -CO-$R^1$,
$R^1$ is a saturated or unsaturated, linear or branched, cyclic or acyclic, C1-C12 unsubstituted hydrocarbon group,
X forms a phosphate group together with O that is bonded to X,
Y is a hydroxy group, and
Z is a hydrogen atom or a hydroxy group.

22. The single stranded oligonucleotide according to claim 21, wherein, in Formula (I), R is a cyano group, and Z is a hydrogen atom.

23. A single stranded photoresponsive nucleic acid with suppressed self-crosslinking ability comprising:

a first base sequence, the first base sequence comprising a modified nucleotide having a structure corresponding to the monomer of Formula (II) or an amino acid analogue of a nucleotide having a structure corresponding to the monomer of Formula (III):

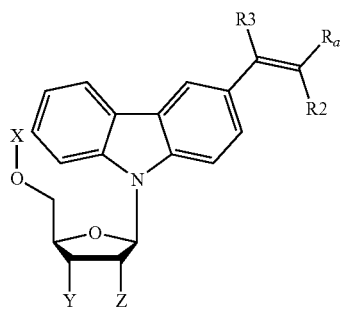
(II)

wherein, in Formula II, $R_a$ is a cyano group, a carboxy group, a C2-C7 alkoxycarbonyl group, or a hydrogen atom, $R_2$ and $R_3$ are independently a cyano group, a carboxy group, a C2-C7 alkoxycarbonyl group, or a hydrogen atom, X forms a phosphate group together with O that is bonded to X, Y is a hydroxy group, and Z is a hydrogen atom or a hydroxyl group;

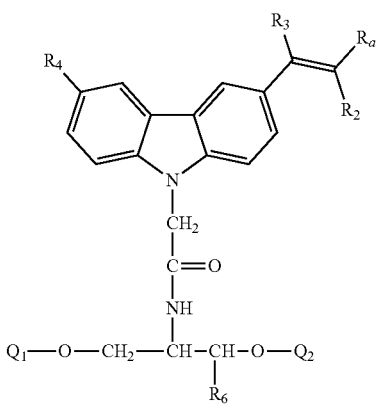
(III)

wherein, in Formula III, $R_a$ is a cyano group, a carboxy group, a C2-C7 alkoxycarbonyl group, a phosphono group, a sulfo group, or a hydrogen atom, $R_2$ and $R_3$ are independently a cyano group, a carboxy group, a C2-C7 alkoxycarbonyl group, or a hydrogen atom, $R_4$ is a hydrogen atom, a hydroxy group, a C1-C3 alkoxy group, a C1-C3 alkylsulfanyl group, a nitro group, a fluorine atom, a fluoromethyl group, a monovalent group of a C6-C12 monocyclic or dicyclic aromatic group, a monovalent group of a monocyclic or dicyclic, naphthyl group, indolyl group, benzoimidazolyl group, benzothiophenyl group or a monovalent group of a formula:

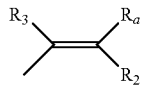

wherein $R_a$, $R_2$, and $R_3$ are independent of $R_a$, $R_2$, and $R_3$ as defined for Formula III and are selected from the groups given above as examples of $R_a$, $R_2$, and $R_3$ for Formula III, $R_6$ is a hydrogen atom, a methyl group, or an ethyl group, $Q_1$ forms a phosphate group together with O that is bonded to $Q_1$, and $Q_2$ is a hydrogen atom, and wherein the modified nucleotide having the structure corresponding to the monomer of Formula (II) or the amino acid analogue of the nucleotide having the structure corresponding to the monomer of Formula (III) is introduced into a base sequence fraction as a base portion of the modified nucleotide of having the structure corresponding to the monomer of Formula (II) or the amino acid analogue of the nucleotide having the structure corresponding to the monomer of Formula (III) by a phosphodiester bond, and a second base sequence, the second base sequence comprising a modified nucleotide having a structure corresponding to the monomer of Formula (I):

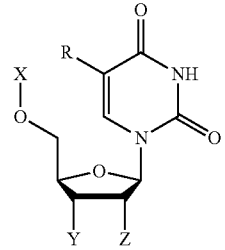
(I)

wherein, in Formula I:

R is -CN or -CO-$R^1$, $R^1$ is a saturated or unsaturated, linear or branched, cyclic or acyclic, C1-C12 hydrocarbon group, X forms a phosphate group together with O that is bonded to X, Y is a hydroxy group, and Z is a hydrogen atom or a hydroxy group.

24. The single stranded photoresponsive nucleic acid with suppressed self-crosslinking ability according to claim 23, wherein R in Formula (I) is a cyano group.

25. The single stranded photoresponsive nucleic acid with suppressed self-crosslinking ability according to claim 24, wherein R is a cyano group, and Z is a hydrogen atom.

26. The single stranded photoresponsive nucleic acid with suppressed self-crosslinking ability according to claim 25, wherein each of the first base sequence and the second base sequence comprises 4 or more bases.

27. The single stranded photoresponsive nucleic acid with suppressed self-crosslinking ability according to claim 25, wherein every nucleotide containing T or U in the sequence of the single stranded photoresponsive nucleic acid with suppressed self-crosslinkable ability is substituted with the modified nucleotide having the structure corresponding to the monomer of Formula (I).

28. The single stranded photoresponsive nucleic acid with suppressed self-crosslinking ability according to claim 24, wherein either:
   1) in Formula (II), $R_a$ is a cyano group, $R_2$ and $R_3$ are hydrogen atoms, and Z is a hydrogen atom, or
   2) in Formula (III), $R_a$ is a cyano group, $R_2$, $R_3$ and $R_4$ are hydrogen atoms, $R_6$ is a methyl group, and $Q_2$ is a hydrogen atom.

29. The single stranded photoresponsive nucleic acid with suppressed self-crosslinking ability according to claim 28, wherein each of the first base sequence and the second base sequence comprises 4 or more bases.

30. The single stranded photoresponsive nucleic acid with suppressed self-crosslinking ability according to claim 28, wherein every nucleotide containing T or U in the sequence of the single stranded photoresponsive nucleic acid with suppressed self-crosslinkable ability is substituted with the modified nucleotide having the structure corresponding to the monomer of Formula (I).

31. The single stranded photoresponsive nucleic acid with suppressed self-crosslinking ability according to claim 24, wherein R is a cyano group, and Z is a hydrogen atom, wherein either:
   1) in Formula (II), $R_a$ is a cyano group, $R_2$ and $R_3$ are hydrogen atoms, and Z is a hydrogen atom, or
   2) in Formula (III), $R_a$ is a cyano group, $R_2$, $R_3$ and $R_4$ are hydrogen atoms, $R_6$ is a methyl group, and $Q_2$ is a hydrogen atom.

32. The single stranded photoresponsive nucleic acid with suppressed self-crosslinking ability according to claim 31, wherein each of the first base sequence and the second base sequence comprises 4 or more bases.

33. The single stranded photoresponsive nucleic acid with suppressed self-crosslinking ability according to claim 31, wherein every nucleotide containing T or U in the sequence of the single stranded photoresponsive nucleic acid with suppressed self-crosslinkable ability is substituted with the modified nucleotide having the structure corresponding to the monomer of Formula (I).

34. The single stranded photoresponsive nucleic acid with suppressed self-crosslinking ability according to claim 24, wherein each of the first base sequence and the second base sequence comprises 4 or more bases.

35. The single stranded photoresponsive nucleic acid with suppressed self-crosslinking ability according to claim 24, wherein every nucleotide containing T or U in the sequence of the single stranded photoresponsive nucleic acid with suppressed self-crosslinkable ability is substituted with the modified nucleotide having the structure corresponding to the monomer of Formula (I).

36. The single stranded photoresponsive nucleic acid with suppressed self-crosslinking ability according to claim 23, wherein R is a cyano group, and Z is a hydrogen atom.

37. The single stranded photoresponsive nucleic acid with suppressed self-crosslinking ability according to claim 36, wherein each of the first base sequence and the second base sequence comprises 4 or more bases.

38. The single stranded photoresponsive nucleic acid with suppressed self-crosslinking ability according to claim 36, wherein every nucleotide containing T or U in the sequence of the single stranded photoresponsive nucleic acid with suppressed self-crosslinkable ability is substituted with the modified nucleotide having the structure corresponding to the monomer of Formula (I).

39. The single stranded photoresponsive nucleic acid with suppressed self-crosslinking ability according to claim 23, wherein either:
   1) in Formula (II), $R_a$ is a cyano group, $R_2$ and $R_3$ are hydrogen atoms, and Z is a hydrogen atom, or
   2) wherein, in Formula (III), $R_a$ is a cyano group, $R_2$, $R_3$ and $R_4$ are hydrogen atoms, $R_6$ is a methyl group, and $Q_2$ is a hydrogen atom.

40. The single stranded photoresponsive nucleic acid with suppressed self-crosslinking ability according to claim 39, wherein each of the first base sequence and the second base sequence comprises 4 or more bases.

41. The single stranded photoresponsive nucleic acid with suppressed self-crosslinking ability according to claim 39, wherein every nucleotide containing T or U in the sequence of the single stranded photoresponsive nucleic acid with suppressed self-crosslinkable ability is substituted with the modified nucleotide having the structure corresponding to the monomer of Formula (I).

42. The single stranded photoresponsive nucleic acid with suppressed self-crosslinking ability according to claim 23, wherein each of the first base sequence and the second base sequence comprises 4 or more bases.

43. The single stranded photoresponsive nucleic acid with suppressed self-crosslinking ability according to claim 23, wherein every nucleotide containing T or U in the sequence of the single stranded photoresponsive nucleic acid with suppressed self-crosslinkable ability is substituted with the modified nucleotide having the structure corresponding to the monomer of Formula (I).

44. A method of hybridizing nucleic acid sequences, comprising:
   performing a hybridizing reaction of a second oligonucleotide with a first oligonucleotide by mixing a first base sequence fraction including the first oligonucleotide with a second base sequence fraction including the second oligonucleotide, the second oligonucleotide comprising a modified nucleotide having a structure corresponding to the monomer of Formula (I):

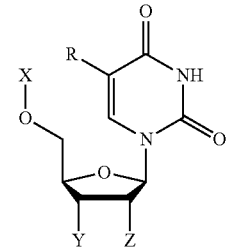

(I)

wherein, in Formula I:
R is -CN or -CO-$R^1$,
$R^1$ is a saturated or unsaturated, linear or branched, cyclic or acyclic, C1-C12 hydrocarbon group,
X forms a phosphate group together with O that is bonded to X,
Y is a hydroxy group, and
Z is a hydrogen atom or a hydroxy group,
wherein the modified nucleotide having a structure corresponding to the monomer of Formula (I) replaces at least one constituent nucleotide which is the photocrosslinkable thymine (T) or uracil (U),
the first oligonucleotide comprising a modified nucleotide having a structure corresponding to the monomer of Formula (II) or an amino acid analogue of a nucleotide having a structure corresponding to the monomer of Formula (III):

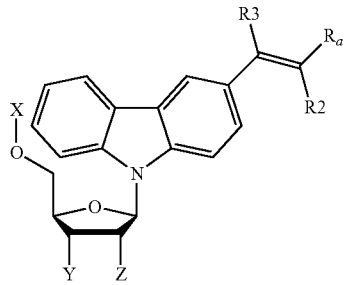
(II)

wherein, in Formula II, $R_a$ is a cyano group, a carboxy group, a C2-C7 alkoxycarbonyl group, or a hydrogen atom, $R_2$ and $R_3$ are independently a cyano group, a carboxy group, a C2-C7 alkoxycarbonyl group, or a hydrogen atom, X forms a phosphate group together with O that is bonded to X, Y is a hydroxy group, and Z is a hydrogen atom or a hydroxyl group;

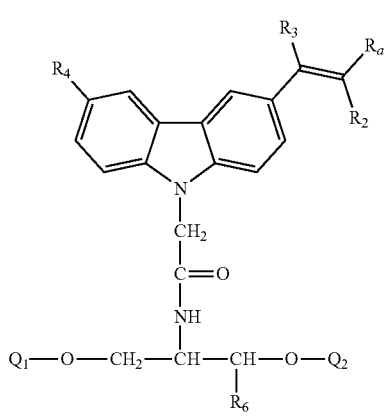
(III)

wherein, in Formula III, $R_a$ is a cyano group, a carboxy group, a C2-C7 alkoxycarbonyl group, a phosphono group, a sulfo group, or a hydrogen atom, $R_2$ and $R_3$ are independently a cyano group, a carboxy group, a $C_2$-C7 alkoxycarbonyl group, or a hydrogen atom, $R_4$ is a hydrogen atom, a hydroxy group, a C1-C3 alkoxy group, a C1-C3 alkylsulfanyl group, a nitro group, a fluorine atom, a fluoromethyl group, a monovalent group of a C6-C12 monocyclic or dicyclic aromatic group, a naphthyl group, an indolyl group, a benzoimidazolyl group, a benzothiophenyl group, or a monovalent group of a formula:

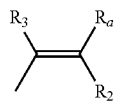

wherein $R_a$, $R_2$, and $R_3$ are independent of $R_a$, $R_2$, and $R_3$ as defined for Formula III and are selected from the groups given above as examples of $R_a$, $R_2$, and $R_3$ for Formula III, $R_6$ is a hydrogen atom, a methyl group, or an ethyl group, $Q_1$ forms a phosphate group together with O that is bonded to $Q_1$, and $Q_2$ is a hydrogen atom, and wherein the modified nucleotide having the structure corresponding to the monomer of Formula (II) or the amino acid analogue of the nucleotide having the structure corresponding to the monomer of Formula (III) is introduced into the second base sequence fraction as a base portion of the modified nucleotide having the structure corresponding to the monomer of Formula (II) or the amino acid analogue of the nucleotide having the structure corresponding to the monomer of Formula (III) by a phosphodiester bond, and wherein the first oligonucleotide is at least partially complementary to the second oligonucleotide sequence fraction.

45. The method of hybridizing nucleic acid sequences according to claim 44, wherein the first oligonucleotide contains the modified nucleotide having the structure corresponding to the monomer of Formula (I), and wherein the modified nucleotide having the structure corresponding to the monomer of Formula (I) replaces at least one constituent nucleotide which is the photocrosslinkable thymine (T) or uracil (U).

46. The method of hybridizing nucleic acid sequences according to claim 45, wherein, in Formula (I), R is a cyano group, and Z is a hydrogen atom.

47. The method of hybridizing nucleic acid sequences according to claim 45, wherein either:

1) in Formula (II), $R_a$ is a cyano group, $R_2$ and $R_3$ are hydrogen atoms, and Z is a hydrogen atom, or 2) in Formula (III), $R_a$ is a cyano group, $R_2$, $R_3$ and $R_4$ are hydrogen atoms, and $R_6$ is a methyl group, and $Q_2$ is a hydrogen atom.

48. The method of hybridizing nucleic acid sequences according to claim 44, wherein, in Formula (I), R is a cyano group, and Z is a hydrogen atom.

49. The method of hybridizing nucleic acid sequences according to claim 44, wherein either:

1) in Formula (II), $R_a$ is a cyano group, $R_2$ and $R_3$ are hydrogen atoms, and Z is a hydrogen atom, or 2) in Formula (III), $R_a$ is a cyano group, $R_2$, $R_3$ and $R_4$ are hydrogen atoms, and $R_6$ is a methyl group, and $Q_2$ is a hydrogen atom.

50. The method of hybridizing nucleic acid sequences according to claim 44,
wherein, in Formula (I), R is a cyano group, and Z is a hydrogen atom, and
wherein, either
1) in Formula (II), $R_a$ is a cyano group, $R_2$ and $R_3$ are hydrogen atoms, and Z is a hydrogen atom, or
2) in Formula (III), $R_a$ is a cyano group, $R_2$, $R_3$ and $R_4$ are hydrogen atoms, $R_6$ is a methyl group, and $Q_2$ is a hydrogen atom.

* * * * *

SEQUENCE LISTING

```
<160> NUMBER OF SEQ ID NOS: 6

<210> SEQ ID NO 1
<211> LENGTH: 12
<212> TYPE: DNA
<213> ORGANISM: Artificial Sequence
<220> FEATURE:
<223> OTHER INFORMATION: ODN 4
<220> FEATURE:
<223> OTHER INFORMATION: Inventor: FUJIMOTO, Kenzo
     Inventor: NAKAMURA, Shigetaka
<220> FEATURE:
<221> NAME/KEY: misc_feature
<222> LOCATION: (4)..(4)
<223> OTHER INFORMATION: n is 3-cyanovinylcarbazole nucleotide

<400> SEQUENCE: 1
gtanagagtg ta                                                        12

<210> SEQ ID NO 2
<211> LENGTH: 12
```

```
<212> TYPE: DNA
<213> ORGANISM: Artificial Sequence
<220> FEATURE:
<223> OTHER INFORMATION: ODN 5
<220> FEATURE:
<221> NAME/KEY: misc_feature
<222> LOCATION: (2)..(2)
<223> OTHER INFORMATION: n is 5-cyano-2'-deoxyuridine
<220> FEATURE:
<221> NAME/KEY: misc_feature
<222> LOCATION: (4)..(4)
<223> OTHER INFORMATION: n is 3-cyanovinylcarbazole nucleotide
<220> FEATURE:
<221> NAME/KEY: misc_feature
<222> LOCATION: (9)..(9)
<223> OTHER INFORMATION: n is 5-cyano-2'-deoxyuridine
<220> FEATURE:
<221> NAME/KEY: misc_feature
<222> LOCATION: (11)..(11)
<223> OTHER INFORMATION: n is 5-cyano-2'-deoxyuridine

<400> SEQUENCE: 2
gnanagagng na                                                         12

<210> SEQ ID NO 3
<211> LENGTH: 20
<212> TYPE: DNA
<213> ORGANISM: Artificial Sequence
<220> FEATURE:
<223> OTHER INFORMATION: ODN 6

<400> SEQUENCE: 3
agagtacact ctatactgag                                                 20

<210> SEQ ID NO 4
<211> LENGTH: 9
<212> TYPE: DNA
<213> ORGANISM: Artificial Sequence
<220> FEATURE:
<223> OTHER INFORMATION: ODN 1
<220> FEATURE:
<221> NAME/KEY: misc_feature
<222> LOCATION: (5)..(5)
<223> OTHER INFORMATION: n is 3-cyanovinylcarbazole nucleotide

<400> SEQUENCE: 4 tgcanacgt                                                              9

<210> SEQ ID NO 5
<211> LENGTH: 9
<212> TYPE: DNA
<213> ORGANISM: Artificial Sequence
<220> FEATURE:
<223> OTHER INFORMATION: ODN 2

<400> SEQUENCE: 5 acgtgtgca                                                              9

<210> SEQ ID NO 6
<211> LENGTH: 9
<212> TYPE: DNA
<213> ORGANISM: Artificial Sequence
<220> FEATURE:
<223> OTHER INFORMATION: ODN 3
<220> FEATURE:
```

```
<221> NAME/KEY: misc_feature
<222> LOCATION: (6)..(6)
<223> OTHER INFORMATION: n is 5-cyano-2'-deoxyuridine

<400> SEQUENCE: 6 acgtgngca                                                              9
```